(12) United States Patent
Perkins et al.

(10) Patent No.: US 9,371,577 B2
(45) Date of Patent: Jun. 21, 2016

(54) FABRICATION OF INTEGRATED COMPUTATIONAL ELEMENTS USING SUBSTRATE SUPPORT SHAPED TO MATCH SPATIAL PROFILE OF DEPOSITION PLUME

(71) Applicant: HALLIBURTON ENERGY SERVICES, INC., Houston, TX (US)

(72) Inventors: David L. Perkins, The Woodlands, TX (US); Robert Paul Freese, Pittsboro, NC (US); Christopher Michael Jones, Houston, TX (US); Richard Neal Gardner, Raleigh, NC (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/400,859

(22) PCT Filed: Mar. 14, 2014

(86) PCT No.: PCT/US2014/029196
§ 371 (c)(1),
(2) Date: Nov. 13, 2014

(87) PCT Pub. No.: WO2015/102657
PCT Pub. Date: Jul. 9, 2015

(65) Prior Publication Data
US 2015/0337435 A1 Nov. 26, 2015

(30) Foreign Application Priority Data
Dec. 31, 2013 (WO) ................ PCT/US2013/078496

(51) Int. Cl.
*C23C 14/50* (2006.01)
*C23C 14/24* (2006.01)
(Continued)

(52) U.S. Cl.
CPC ............. *C23C 14/505* (2013.01); *C23C 14/24* (2013.01); *C23C 14/50* (2013.01); *C23C 14/54* (2013.01);
(Continued)

(58) Field of Classification Search
None
See application file for complete search history.

(56) References Cited

U.S. PATENT DOCUMENTS

| 4,380,212 A * | 4/1983 | Kraus | ................... C23C 14/044 |
| | | | 118/504 |
| 4,516,525 A * | 5/1985 | Bourgeois | ............... C23C 14/30 |
| | | | 118/688 |

(Continued)

FOREIGN PATENT DOCUMENTS

| WO | WO 2004/015364 | 2/2004 |
| WO | WO 2006/031733 | 3/2006 |

(Continued)

OTHER PUBLICATIONS

International Search Report and Written Opinion of the International Searching Authority issued in International Application No. PCT/US2014/029196 on Sep. 26, 2014; 10 pages.

(Continued)

*Primary Examiner* — Binu Thomas
(74) *Attorney, Agent, or Firm* — Benjamin Fite; Fish & Richardson P.C.

(57) ABSTRACT

A system includes a computational system to receive a design of an integrated computational element (ICE) including specification of a substrate and a plurality of layers, their respective target thicknesses and complex indices, such that a notional ICE fabricated based on the ICE design is related to a characteristic of a sample. Additionally, the system includes a deposition chamber including a deposition source to provide a deposition plume having a plume spatial profile, and a support to support a plurality of instances of the substrate during fabrication of a plurality of instances of the ICE. The support is spaced apart from the deposition source and has a shape that corresponds to the plume spatial profile, such that when the supported instances of the substrate are distributed over the support, thicknesses of instances of each of the deposited layers are substantially uniform across the plurality of instances of the ICE.

15 Claims, 9 Drawing Sheets

(51) Int. Cl.

| | |
|---|---|
| C23C 16/00 | (2006.01) |
| C23C 14/54 | (2006.01) |
| G01N 21/25 | (2006.01) |
| E21B 47/00 | (2012.01) |
| G01J 3/00 | (2006.01) |
| G01N 21/31 | (2006.01) |
| G06E 3/00 | (2006.01) |
| C23C 14/10 | (2006.01) |

(52) U.S. Cl.
CPC .............. *C23C 14/542* (2013.01); *E21B 47/00* (2013.01); *G01J 3/00* (2013.01); *G01N 21/25* (2013.01); *G01N 21/31* (2013.01); *G06E 3/001* (2013.01); *C23C 14/10* (2013.01); *G01N 2021/317* (2013.01)

(56) References Cited

U.S. PATENT DOCUMENTS

| 4,858,556 | A | * | 8/1989 | Siebert | C23C 14/546 118/664 |
|---|---|---|---|---|---|
| 5,075,550 | A | | 12/1991 | Miller et al. | |
| 5,399,229 | A | | 3/1995 | Stefani et al. | |
| 5,453,716 | A | | 9/1995 | Person et al. | |
| 5,537,479 | A | | 7/1996 | Kreisel et al. | |
| 5,619,366 | A | | 4/1997 | Rhoads et al. | |
| 6,078,389 | A | | 6/2000 | Zetter | |
| 6,082,296 | A | * | 7/2000 | Tran | C23C 14/24 118/723 EB |
| 6,154,550 | A | | 11/2000 | Beyer | |
| 6,163,259 | A | | 12/2000 | Barsumian et al. | |
| 6,168,832 | B1 | * | 1/2001 | Boucher | C23C 14/044 204/192.1 |
| 6,198,531 | B1 | | 3/2001 | Myrick et al. | |
| 6,213,250 | B1 | | 4/2001 | Wisniewski et al. | |
| 6,529,276 | B1 | | 3/2003 | Myrick | |
| 6,646,753 | B2 | | 11/2003 | Zhang et al. | |
| 6,804,060 | B1 | | 10/2004 | Tsai et al. | |
| 6,905,578 | B1 | | 6/2005 | Moslehi et al. | |
| 6,965,431 | B2 | | 11/2005 | Vo-Dinh et al. | |
| 7,138,156 | B1 | | 11/2006 | Myrick et al. | |
| 7,163,901 | B2 | | 1/2007 | Downey | |
| 7,332,044 | B2 | | 2/2008 | Sidorin et al. | |
| 7,679,563 | B2 | | 3/2010 | Werner et al. | |
| 7,697,141 | B2 | | 4/2010 | Jones et al. | |
| 7,753,847 | B2 | | 7/2010 | Greenleaf et al. | |
| 7,777,870 | B2 | | 8/2010 | Hayes et al. | |
| 7,792,644 | B2 | | 9/2010 | Kotter et al. | |
| 7,828,929 | B2 | | 11/2010 | Lee et al. | |
| 7,911,605 | B2 | | 3/2011 | Myrick et al. | |
| 7,920,258 | B2 | | 4/2011 | Myrick et al. | |
| 8,054,212 | B1 | | 11/2011 | Holly et al. | |
| 8,106,850 | B1 | | 1/2012 | Gregoire et al. | |
| 8,164,061 | B2 | | 4/2012 | Pawlak et al. | |
| 8,216,161 | B2 | | 7/2012 | Darlington et al. | |
| 8,252,112 | B2 | | 8/2012 | Ovshinsky | |
| 2005/0054928 | A1 | | 3/2005 | Cerofolini | |
| 2007/0090091 | A1 | * | 4/2007 | Adomaitis | C23C 14/542 118/715 |
| 2009/0047416 | A1 | * | 2/2009 | Ohbayashi | C23C 14/243 118/665 |
| 2009/0169766 | A1 | * | 7/2009 | Takahashi | C23C 14/32 118/723 FI |
| 2009/0182693 | A1 | | 7/2009 | Fulton et al. | |
| 2009/0213381 | A1 | | 8/2009 | Appel et al. | |
| 2010/0245096 | A1 | | 9/2010 | Jones et al. | |
| 2012/0150451 | A1 | | 6/2012 | Skinner et al. | |
| 2012/0268744 | A1 | | 10/2012 | Wolf et al. | |
| 2013/0284894 | A1 | | 10/2013 | Freese et al. | |
| 2013/0284895 | A1 | | 10/2013 | Freese et al. | |
| 2013/0284896 | A1 | | 10/2013 | Freese et al. | |
| 2013/0284897 | A1 | | 10/2013 | Freese et al. | |
| 2013/0284898 | A1 | | 10/2013 | Freese et al. | |
| 2013/0284899 | A1 | | 10/2013 | Freese et al. | |
| 2013/0284900 | A1 | | 10/2013 | Freese et al. | |
| 2013/0284901 | A1 | | 10/2013 | Freese et al. | |
| 2013/0284904 | A1 | | 10/2013 | Freese et al. | |
| 2013/0286398 | A1 | | 10/2013 | Freese et al. | |
| 2013/0287061 | A1 | | 10/2013 | Freese et al. | |

FOREIGN PATENT DOCUMENTS

| WO | WO 2007/015115 | 2/2007 |
|---|---|---|
| WO | WO 2011/103066 | 8/2011 |
| WO | WO 2013/022556 | 2/2013 |

OTHER PUBLICATIONS

Frey et al., "Temperature-dependent refractive index of silicon and germanium," NASA Goodard Space Flight Center, Greenbelt, MD, 2006, 10 pages.

Morton et al., "Optical Monitoring of Thin-films Using Spectroscopic Ellipsometry," Society of Vacuum Coaters, 45th Annual Technical Conference Proceedings, 2002, 7 pages.

Eastwood et al., "Filed applications of stand-off sensing using visible/NIR multivariate optical computing," Department of Chemistry and Biochemistry, University of South Carolina, SPE vol. 4199, 2001, 10 pages.

Paul et al., "Fabrication of mid-infrared frequency-selective surfaces by soft lithography", Applied Optics, v. 40, No. 25, Sep. 2001, 5 pages.

Haibach et al., "Precision in multivariate optical computing," Applied Optics, vol. 43, No. 10, Apr. 1, 2004, 11 pages.

J.A. Woollam Co., Inc., Characterizing Processes with EASE® In Situ Applications, Application Note, 2009, 3 pages.

Li, "Refractive Index of Silicon and Germanium and Its Wavelength and Temperature Derivatives," Center for Information and Numerical Data Analysis and Synthesis, Purdue University, J. Phys. Chem. Ref. Data, vol. 9, No. 3, 1980, 98 pages.

Myrick, "Multivariate optical elements simplify spectroscopy," Laser Focus World, Mar. 1, 2002, access date Feb. 28, 2013, 3 pages http://www.laserfocusworld.com/articles/print/volume-38/issue-3/features/spectroscopy/multivariate-optical-elements-simplify-spectroscopy.html.

Myrick et al., "A single-element all-optical approach to chemometric prediction," Vibrational Spectroscopy 28, 2002, 9 pages.

Myrick et al., "Spectral tolerance determination for multivariate optical element design," Fresenius J Anal Chem, 369, 2001, 5 pages.

Myrick et al., "Application of multivariate optical computing to simple near-infrared point measurements," SPIE vol. 4574, Department of Chemistry and biochemistry, University of South Carolina, 2002, 8 pages.

Rabady et al., "High-resolution photometric optical monitoring for thin-film deposition," Applied Optics, Optical Society of America, vol. 43, No. 1, Jan. 1, 2004, 6 pages.

Priore et al., "Novel Imaging Systems: Multivariate Optical Computing in the UV-VIS," Department of Chemistry and Biochemistry, University of South Carolina, 2003, 5 pages.

Grader et al., "Fourier transform infrared spectroscopy of a single aerosol particle," J. Chem. Phys. 86 (11), Jun. 1, 1987, 7 pages.

Soyemi et al., "Novel Filter Design Algorithm for Multivariate Optical Computing," Advanced Environmental and Chemical Sensing Technology, SPIE vol. 4205, 2001, 12 pages.

Telemark, "Model 820 In-Situ Spectroscopic Optical Monitor," Dec. 2010, 4 pages.

Bossard et al., "The Design and fabrication of planar multiband metallodielectric frequency selective surfaces for infrared applications", IEEE Trans. on Antennas and Propagation, v. 50, No. 4, Apr. 2006, 12 pages.

Woollam et al., "Overview of Variable Angle Spectroscopic Ellipsometer (VASE), Part 1: Basic Theory and Typical Applications," Society of Photo-Optical Instrumentation Engineers, Critical Reviews of Optical Science Technology CR72, 1999, 28 pages.

Zoeller et al., "Substantial progress in optical monitoring by intermittent measurement technique," SPIE, Published in the processing of the OSD, Jena 2005, vol. 5963-13, 9 pages.

* cited by examiner

US 9,371,577 B2

FABRICATION OF INTEGRATED COMPUTATIONAL ELEMENTS USING SUBSTRATE SUPPORT SHAPED TO MATCH SPATIAL PROFILE OF DEPOSITION PLUME

CLAIM OF PRIORITY

This application is a U.S. National Stage of International Application No. PCT/US2014/029196, filed Mar. 14, 2014, which claims priority to International Application No. PCT/US2013/078496, filed Dec. 31, 2013, the entire contents of which are hereby incorporated by reference.

BACKGROUND

The subject matter of this disclosure is generally related to fabrication of an integrated computational element (ICE) used in optical analysis tools for analyzing a substance of interest, for example, crude petroleum, gas, water, or other wellbore fluids. For instance, the disclosed ICE fabrication uses a support for formed layers of ICEs, where the support is shaped and arranged relative to a deposition source used to form the layers such that a shape of the support corresponds to a spatial profile of a deposition plume provided by the deposition source.

Information about a substance can be derived through the interaction of light with that substance. The interaction changes characteristics of the light, for instance the frequency (and corresponding wavelength), intensity, polarization, and/or direction (e.g., through scattering, absorption, reflection or refraction). Chemical, thermal, physical, mechanical, optical or various other characteristics of the substance can be determined based on the changes in the characteristics of the light interacting with the substance. As such, in certain applications, one or more characteristics of crude petroleum, gas, water, or other wellbore fluids can be derived in-situ, e.g., downhole at well sites, as a result of the interaction between these substances and light.

Integrated computational elements (ICEs) enable the measurement of various chemical or physical characteristics through the use of regression techniques. An ICE selectively weights, when operated as part of optical analysis tools, light modified by a sample in at least a portion of a wavelength range such that the weightings are related to one or more characteristics of the sample. An ICE can be an optical substrate with multiple stacked dielectric layers (e.g., from about 2 to about 50 layers), each having a different complex refractive index from its adjacent layers. The specific number of layers, N, the optical properties (e.g. real and imaginary components of complex indices of refraction) of the layers, the optical properties of the substrate, and the physical thickness of each of the layers that compose the ICE are selected so that the light processed by the ICE is related to one or more characteristics of the sample. Because ICEs extract information from the light modified by a sample passively, they can be incorporated in low cost and rugged optical analysis tools. Hence, ICE-based downhole optical analysis tools can provide a relatively low cost, rugged and accurate system for monitoring quality of wellbore fluids, for instance.

Errors in fabrication of the constituent layers of an ICE can degrade the ICE's target performance. In most cases, deviations of <0.1% and even 0.01% or 0.0001% from point by point design values of the complex indices of refraction, and/or thicknesses of the formed layers of the ICE can substantially degrade the ICE's performance, in some cases to such an extent, that the ICE becomes operationally useless.

Those familiar or currently practicing in the art will readily appreciate that the ultra-high accuracies required by ICE designs challenge the state of the art in thin film deposition techniques. Conventionally, a support (sometimes referred to as a platen) that supports ICEs within the field of view of a deposition source is spaced apart therefrom and has a flat shape. Moreover, a size of the deposition source is typically smaller than a size of the flat support. In such cases, when an azimuthal axis of the deposition source intersects the center of the flat support, non-uniformities of deposition rates across the flat support are induced because a distance from the deposition source to ICEs supported near the center of the flat support is shorter than a distance from the deposition source to the ICEs supported near the edge of the flat support, and, thus more material is deposited per unit time at the center than at the edge.

DESCRIPTION OF DRAWINGS

Like reference symbols in the various drawings indicate like elements.

DETAILED DESCRIPTION

Technologies are described for fabricating ICEs using a support for supporting formed layers of ICEs, where the support is shaped and arranged relative to a deposition source used to form the layers such that a shape of the support corresponds to a spatial profile of a deposition plume provided by the deposition source. For example, substrates of the ICEs are distributed on a support shaped like a portion of a sphere whose radius of curvature is the same as the distance from a deposition point-source to the support. In this manner, deposition rates and the resulting optical (e.g., complex refractive indices) and physical (e.g., thicknesses) characteristics of the formed ICE layers are the same everywhere on the portion of the sphere. Other support shapes can be employed to take into account spatial profiles of deposition sources that are not point-source, such as distributed or extended deposition sources.

The disclosed technologies can be used to implement ICE fabrication that can be more accurate than conventional ICE fabrication. For instance, distributing, during deposition, multiple substrates of ICEs in a fabrication batch on a support having a shape that matches the spatial profile of the deposition plume, results in obtaining optical (e.g., complex refractive indices) and physical (e.g., thicknesses) characteristics of the formed layers that constitute the ICEs that are uniform over the fabrication batch. This may lead to increased ICE fabrication yield for a batch fabricated according to the disclosed technologies relative to conventional ICE fabrication where a shape of the support used during deposition is not matched to the spatial profile of the deposition plume. Moreover, because the layer characteristics are expected to be uniform for the ICEs distributed over the disclosed support, a number of locations of the support at which the layer characteristics are monitored can be reduced relative to conventional ICE fabrication. As such, for some support spatial profiles, the layer characteristics monitored at a single location may be representative for the entire fabrication batch, such that monitoring at the single location is sufficient to characterize the entire ICE fabrication batch.

Prior to describing example implementations of the disclosed technologies for ICE fabrication, the following technologies are described below: in Section (1)—optical analysis tools based on ICE along with examples of their use in oil/gas exploration, and in Section (2)—techniques for designing an ICE.

(1) ICE-Based Analysis of Wellbore Fluids

Figure 1A:
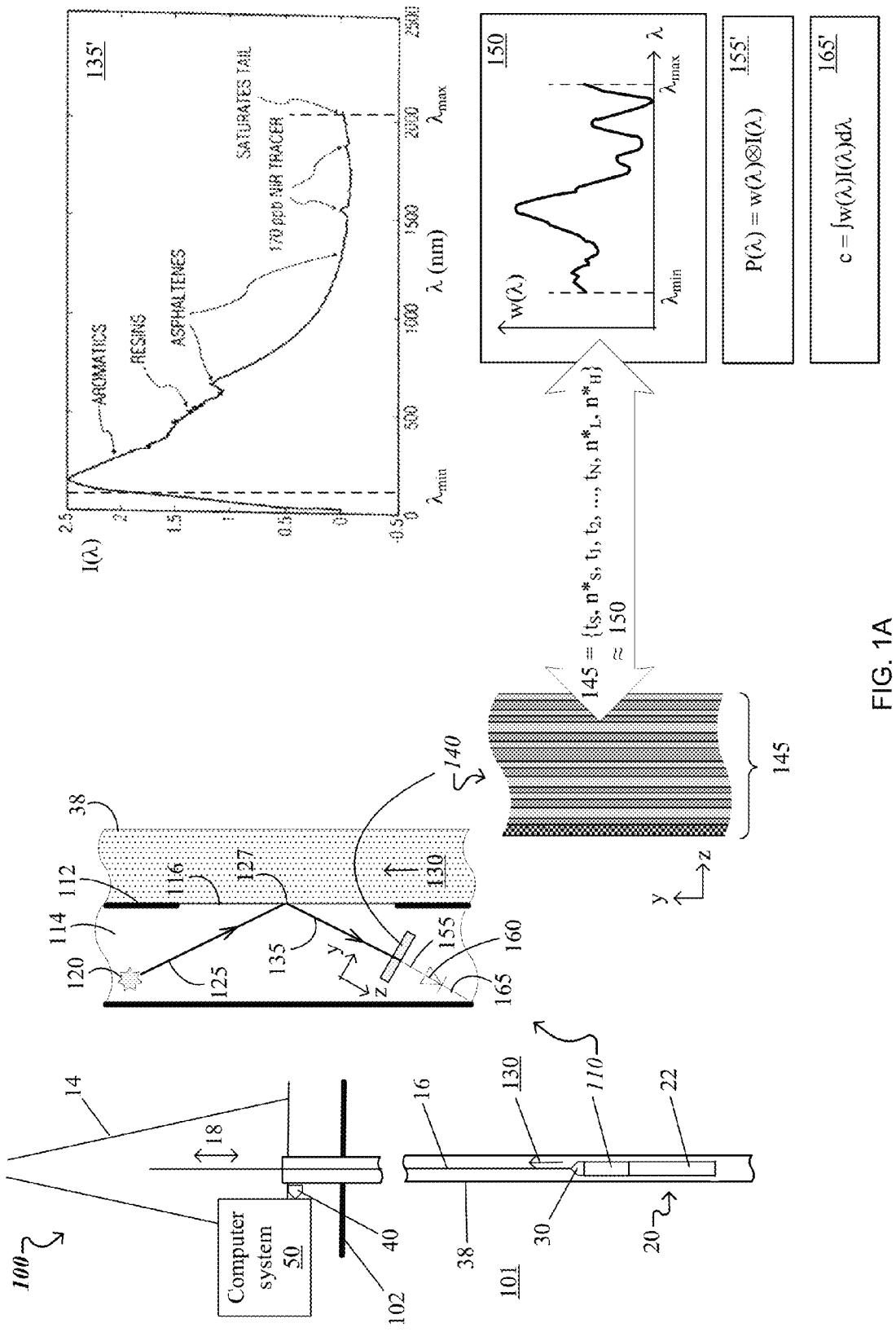
FIGS. 1A-1C show multiple configurations of an example of a system for analyzing wellbore fluids that uses a well logging tool including an ICE.
Figure 1C:
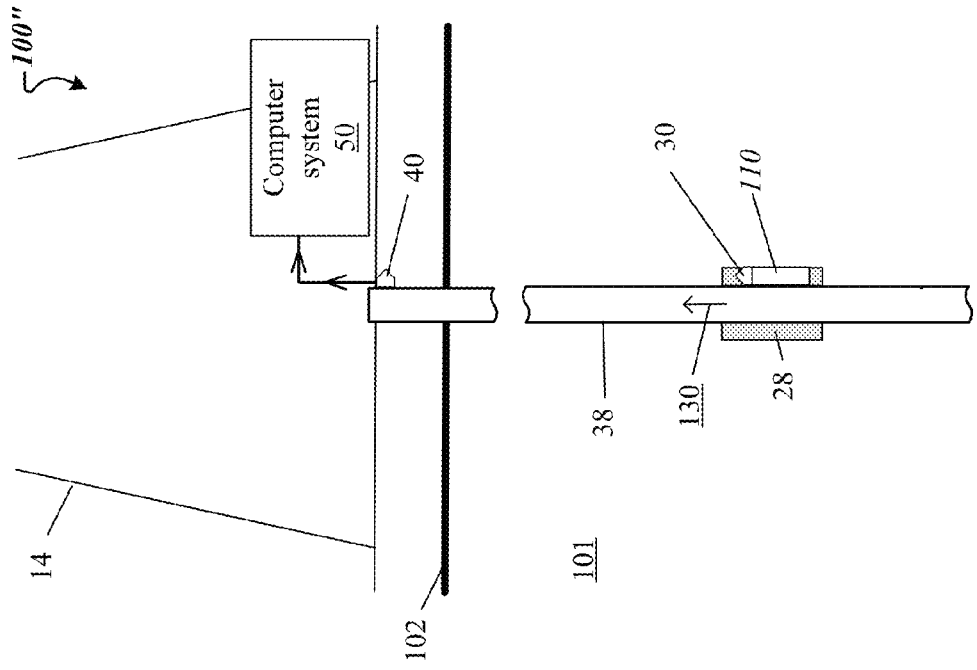
Figure 1B:
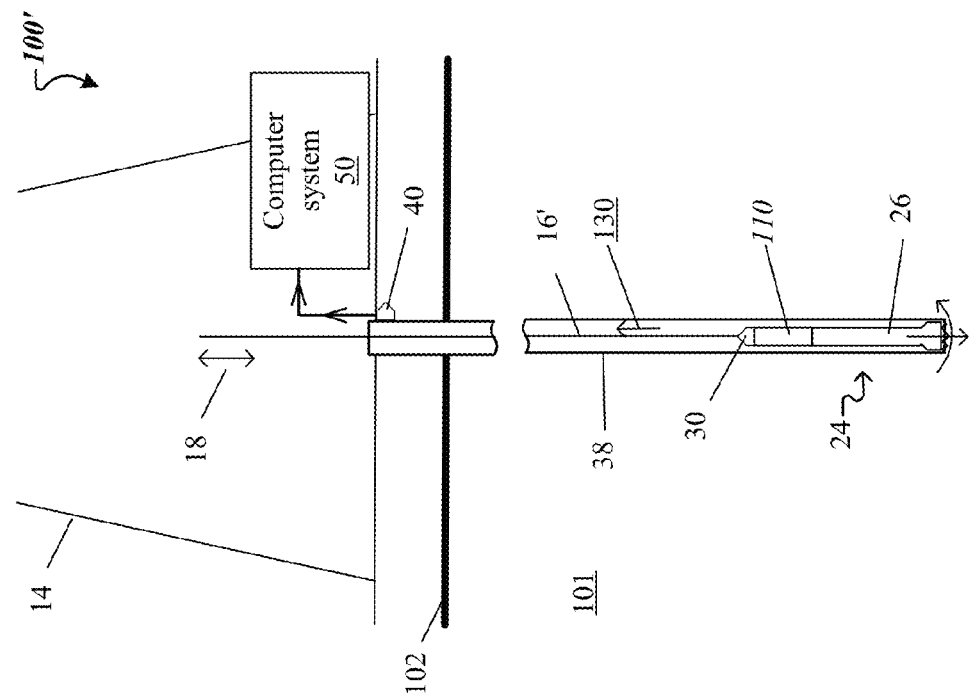

FIGS. 1A-1C show multiple configurations 100, 100', 100" of an example of a system for analyzing wellbore fluids 130, such that analyses are generated from measurements taken with a well logging tool 110 configured as an ICE-based optical analysis tool. The disclosed system also is referred to as a well logging system.

Each of the configurations 100, 100', 100" of the well logging system illustrated in FIGS. 1A-1C includes a rig 14 above the ground surface 102 and a wellbore 38 below the ground surface. The wellbore 38 extends from the ground surface into the earth 101 and generally passes through multiple geologic formations. In general, the wellbore 38 can contain wellbore fluids 130. The wellbore fluids 130 can be crude petroleum, mud, water or other substances and combinations thereof. Moreover, the wellbore fluids 130 may be at rest, or may flow toward the ground surface 102, for instance. Additionally, surface applications of the well logging tool 110 may include water monitoring and gas and crude transportation and processing.

FIG. 1A shows a configuration 100 of the well logging system which includes a tool string 20 attached to a cable 16 that can be lowered or raised in the wellbore 38 by draw works 18. The tool string 20 includes measurement and/or logging tools to generate and log information about the wellbore fluids 130 in the wellbore 38. In the configuration 100 of the well logging system, this information can be generated as a function of a distance (e.g., a depth) with respect to the ground surface 102. In the example illustrated in FIG. 1A, the tool string 20 includes the well logging tool 110, one or more additional well logging tool(s) 22, and a telemetry transmitter 30. Each of the well logging tools 110 and 22 measures one or more characteristics of the wellbore fluids 130. In some implementations, the well logging tool 110 determines values of the one or more characteristics in real time and reports those values instantaneously as they occur in the flowing stream of wellbore fluids 130, sequentially to or simultaneously with other measurement/logging tools 22 of the tool string 20.

FIG. 1B shows another configuration 100' of the well logging system which includes a drilling tool 24 attached to a drill string 16'. The drilling tool 24 includes a drill bit 26, the ICE-based well logging tool 110 configured as a measurement while drilling (MWD) and/or logging while drilling (LWD) tool, and the telemetry transmitter 30. Drilling mud is provided through the drill string 16' to be injected into the borehole 38 through ports of the drill bit 26. The injected drilling mud flows up the borehole 38 to be returned above the ground level 102, where the returned drilling mud can be resupplied to the drill string 16' (not shown in FIG. 1B). In this case, the MWD/LWD-configured well logging tool 110 generates and logs information about the wellbore fluids 130 (e.g., drilling mud in this case) adjacent the working drill bit 26.

FIG. 1C shows yet another configuration 100" of the well logging system which includes a permanent installation adjacent to the borehole 38. In some implementations, the permanent installation is a set of casing collars that reinforce the borehole 38. In this case, a casing collar 28 from among the set of casing collars supports the well logging tool 110 and the telemetry transmitter 30. In this manner, the well logging tool 110 determines and logs characteristics of the wellbore fluids 130 adjacent the underground location of the casing collar 28.

In each of the above configurations 100, 100' and 100" of the well logging system, the values of the one or more characteristics measured by the well logging tool 110 are provided (e.g., as a detector signal 165) to the telemetry transmitter 30. The latter communicates the measured values to a telemetry receiver 40 located above the ground surface 102. The telemetry transmitter 30 and the telemetry receiver 40 can communicate through a wired or wireless telemetry channel. In some implementations of the system configurations 100, 100' illustrated in FIGS. 1A and 1B, e.g., in slickline or coiled tubing applications, measurement data generated by the well logging tool 110 can be written locally to memory of the well logging tool 110.

The measured values of the one or more characteristics of the wellbore fluids 130 received by the telemetry receiver 40 can be logged and analyzed by a computer system 50 associated with the rig 14. In this manner, the measurement values provided by the well logging tool 110 can be used to generate physical and chemical information about the wellbore fluids 130 in the wellbore 38.

Referring again to FIG. 1A, the well logging tool 110 includes a light source 120, an ICE 140 and an optical transducer 160. The well logging tool 110 has a frame 112 such that these components are arranged in an enclosure 114 thereof. A cross-section of the well logging tool 110 in a plane perpendicular to the page can vary, depending on the space available. For example, the well logging tool's cross-section can be circular or rectangular, for instance. The well logging tool 110 directs light to the sample 130 through an optical interface 116, e.g., a window in the frame 112. The well logging tool 110 is configured to probe the sample 130 (e.g., the wellbore fluids stationary or flowing) in the wellbore 38 through the optical interface 116 and to determine an amount (e.g., a value) of a given characteristic (also referred to as a characteristic to be measured) of the probed sample 130. The characteristic to be measured can be any one of multiple characteristics of the sample 130 including concentration of a given substance in the sample, a gas-oil-ratio (GOR), pH value, density, viscosity, etc.

The light source 120 outputs light with a source spectrum over a particular wavelength range, from a minimum wavelength $\lambda_{min}$ to a maximum wavelength $\lambda_{max}$. In some implementations, the source spectrum can have non-zero intensity over the entire or most of the wavelength range $\lambda_{max}$-$\lambda_{min}$. In some implementations, the source spectrum extends through UV-vis (0.2-0.8 µm) and near-IR (0.8-2.5 µm) spectral ranges. Alternatively, or additionally, the source spectrum extends through near-IR and mid-IR (2.5-25 µm) spectral ranges. In some implementations, the source spectrum extends through near-IR, mid-IR and far-IR (25-100 µm)

spectral ranges. In some implementations, the light source 120 is tunable and is configured in combination with time resolved signal detection and processing.

The light source 120 is arranged to direct a probe beam 125 of the source light towards the optical interface 116 where it illuminates the sample 130 at a location 127. The source light in the probe beam 125 interacts with the sample 130 and reflects off it as light modified by the sample 130. The light modified by the sample has a modified spectrum $I(\lambda)$ 135' over the particular wavelength range. In the reflective configuration of the well logging tool 110 illustrated in FIG. 1A (i.e., where the light to be analyzed reflects at the sample/window interface), the modified spectrum $I(\lambda)$ 135' is a reflection spectrum associated with the sample 130. In a transmission configuration of the well logging tool 110 (not shown in FIG. 1A), the probe beam is transmitted through the sample as modified light, such that the modified spectrum $I(\lambda)$ 135' is a transmission spectrum associated with the sample.

In general, the modified spectrum $I(\lambda)$ 135' encodes information about multiple characteristics associated with the sample 130, and more specifically the encoded information relates to current values of the multiple characteristics. In the example illustrated in FIG. 1A, the modified spectrum 135' contains information about one or more characteristics of the wellbore fluids 130.

With continued reference to FIG. 1A, and the Cartesian coordinate system provided therein for reference, the ICE 140 is arranged to receive a beam 135 of the sample modified light, and is configured to process it and to output a beam 155 of processed light. The beam 135 of sample modified light is incident on a first surface of the ICE 140 along the z-axis, and the beam 155 of processed light is output along the z-axis after transmission through the ICE 140. Alternatively or additionally, the beam 155 (or an additional reflected beam) of processed light can be output after reflection off the first surface of the ICE 140. The ICE 140 is configured to process the sample modified light by weighting it in accordance with an optical spectrum $w(\lambda)$ 150 associated with a characteristic to be measured.

The optical spectrum $w(\lambda)$ 150 is determined offline by applying conventional processes to a set of calibration spectra $I(\lambda)$ of the sample which correspond to respective known values of the characteristic to be measured. As illustrated by optical spectrum $w(\lambda)$ 150, optical spectrums generally may include multiple local maxima (peaks) and minima (valleys) between $\lambda_{min}$ and $\lambda_{max}$. The peaks and valleys may have the same or different amplitudes. For instance, an optical spectrum $w(\lambda)$ can be determined through regression analysis of $N_c$ calibration spectra $I_j(\lambda)$ of a sample, where $j=1, \ldots, N_c$, such that each of the calibration spectra $I_j(\lambda)$ corresponds to an associated known value of a given characteristic for the sample. A typical number $N_c$ of calibration spectra $I_j(\lambda)$ used to determine the optical spectrum $w(\lambda)$ 150 through such regression analysis can be $N_c=10$, 40 or 100, for instance. The regression analysis outputs, within the $N_c$ calibration spectra $I_j(\lambda)$, a spectral pattern that is unique to the given characteristic. The spectral pattern output by the regression analysis corresponds to the optical spectrum $w(\lambda)$ 150. In this manner, when a value of the given characteristic for the sample is unknown, a modified spectrum $I_u(\lambda)$ of the sample is acquired by interacting the probe beam 125 with the sample 130, then the modified spectrum $I_u(L)$ is weighted with the ICE 140 to determine a magnitude of the spectral pattern corresponding to the optical spectrum $w(\lambda)$ 150 within the modified spectrum $I_u(\lambda)$. The determined magnitude is proportional to the unknown value of the given characteristic for the sample.

For example, the sample can be a mixture (e.g., the wellbore fluid 130) containing substances X, Y and Z, and the characteristic to be measured for the mixture is concentration $c_X$ of substance X in the mixture. In this case, $N_c$ calibration spectra $I_j(\lambda)$ were acquired for $N_c$ samples of the mixture having respectively known concentration values for each of the substances contained in the $N_c$ samples. By applying regression analysis to the $N_c$ calibration spectra $I_j(\lambda)$, a first spectral pattern that is unique to the concentration $c_X$ of the X substance can be detected (recognized), such that the first spectral pattern corresponds to a first optical spectrum $w_{cX}(\lambda)$ associated with a first ICE, for example. Similarly, second and third spectral patterns that are respectively unique to concentrations $c_Y$ and $c_Z$ of the Y and Z substances can also be detected, such that the second and third spectral patterns respectively correspond to second and third optical spectra $w_{cY}(\lambda)$ and $w_{cZ}(\lambda)$ respectively associated with second and third ICEs. In this manner, when a new sample of the mixture (e.g., the wellbore fluid 130) has an unknown concentration $c_X$ of the X substance, for instance, a modified spectrum $I_u(\lambda)$ of the new sample can be acquired by interacting the probe beam with the mixture, then the modified spectrum $Iu(\lambda)$ is weighted with the first ICE to determine a magnitude of the first spectral pattern within the modified spectrum $I_u(\lambda)$. The determined magnitude is proportional to the unknown value of the concentration $c_X$ of the X substance for the new sample.

Referring again to FIG. 1A, the ICE 140 includes N layers of materials stacked on a substrate, such that complex refractive indices of adjacent layers are different from each other. The total number of stacked layers can be between 6 and 50, for instance. The substrate material can be BK7, diamond, Ge, ZnSe (or other transparent dielectric material), and can have a thickness in the range of 0.02-2 mm, for instance, to insure structural integrity of the ICE 140.

Throughout this specification, a complex index of refraction (or complex refractive index) $n^*$ of a material has a complex value, $Re(n^*)+iIm(n^*)$. $Re(n^*)$ represents a real component of the complex index of refraction responsible for refractive properties of the material, and $Im(n^*)$ represents an imaginary component of the complex index of refraction (also known as extinction coefficient $\kappa$) responsible for absorptive properties of the material. In this specification, when it is said that a material has a high complex index of refraction $n^*_H$ and another material has a low complex index of refraction $n^*_L$, the real component $Re(n^*_H)$ of the high complex index of refraction $n^*_H$ is larger than the real component $Re(n^*_L)$ of the low complex index of refraction $n^*_L$, $Re(n^*_H) > Re(n^*_L)$. Materials of adjacent layers of the ICE are selected to have a high complex index of refraction $n^*_H$ (e.g., Si), and a low complex index of refraction $n^*_L$ (e.g., $SiO_2$). Here, $Re(n^*_{Si})$ 2.4 > $Re(n^*_{SiO2}) \approx 1.5$. For other material pairings, however, the difference between the high complex refractive index $n^*_H$ and low complex refractive index $n^*_L$ may be much smaller, e.g., $Re(n^*_H) \approx 1.6 > Re(n^*_L) \approx 1.5$. The use of two materials for fabricating the N layers is chosen for illustrative purposes only. For example, a plurality of materials having different complex indices of refraction, respectively, can be used. Here, the materials used to construct the ICE are chosen to achieve a desired optical spectrum $w(\lambda)$ 150.

A set of design parameters 145—which includes the total number of stacked layers N, the complex refractive indices $n^*_H$, $n^*_L$ of adjacent stacked layers, and the thicknesses of the N stacked layers $t(1), t(2), \ldots, t(N-1), t(N)$—of the ICE 140 can be chosen (as described below in connection with FIG. 2) to be spectrally equivalent to the optical spectrum $w(\lambda)$ 150 associated with the characteristic to be measured. As such, an ICE design includes a set 145 of thicknesses $\{t(i), i=1, \ldots, N\}$ of the N layers stacked on the substrate that correspond to the optical spectrum $w(\lambda)$ 150.

In view of the above, the beam 155 of processed light output by the ICE 140 has a processed spectrum $P(\lambda)=w(\lambda) \oplus I(\lambda)$ 155' over the wavelength range $\lambda_{max}$-$\lambda_{min}$, such that the processed spectrum 155' represents the modified spectrum $I(\lambda)$ 135' weighted by the optical spectrum $w(\lambda)$ 150 associated with the characteristic to be measured.

The beam 155 of processed light is directed from the ICE 140 to the optical transducer 160, which detects the processed light and outputs an optical transducer signal 165. A value (e.g., a voltage) of the optical transducer signal 165 is a result of an integration of the processed spectrum 155' over the particular wavelength range and is proportional to the unknown value "c" 165' of the characteristic to be measured for the sample 130.

In some implementations, the well logging tool 110 can include a second ICE (not shown in FIG. 1A) associated with a second ICE design that includes a second set of thicknesses $\{t'(i), i=1, \ldots, N'\}$ of a second total number N' of layers, each having a different complex refractive index from its adjacent layers, the complex refractive indices and the thicknesses of the N' layers corresponding to a second optical spectrum $w'(\lambda)$. Here, the second optical spectrum $w'(\lambda)$ is associated with a second characteristic of the sample 130, and a second processed spectrum represents the modified spectrum $I(\lambda)$ 135' weighted by the second optical spectrum $w'(\lambda)$, such that a second value of a second detector signal is proportional to a value of the second characteristic for the sample 130.

In some implementations, the determined value 165' of the characteristic to be measured can be logged along with a measurement time, geo-location, and other metadata, for instance. In some implementations, the detector signal 165, which is proportional to a characteristic to be measured by the well logging tool 110, can be used as a feedback signal to adjust the characteristic of the sample, to modify the sample or environmental conditions associated with the sample, as desired.

Characteristics of the wellbore fluids 130 that can be related to the modified spectrum 135' through the optical spectra associated with the ICE 140 and other ICEs (not shown in FIG. 1A) are concentrations of one of asphaltene, saturates, resins, aromatics; solid particulate content; hydrocarbon composition and content; gas composition C1-C6 and content: $CO_2$, $H_2S$ and correlated PVT properties including GOR, bubble point, density; a petroleum formation factor; viscosity; a gas component of a gas phase of the petroleum; total stream percentage of water, gas, oil, solid articles, solid types; oil finger printing; reservoir continuity; oil type; and water elements including ion composition and content, anions, cations, salinity, organics, pH, mixing ratios, tracer components, contamination, or other hydrocarbon, gas, solids or water property.

(2) Aspects of Ice Design

Aspects of a process for designing an ICE associated with a characteristic to be measured (e.g., one of the characteristics enumerated above) are described below. Here, an input of the ICE design process is a theoretical optical spectrum $w_{th}(\lambda)$ associated with the characteristic. An output of the ICE design process is an ICE design that includes specification of (1) a substrate and a number N of layers to be formed on the substrate, each layer having a different complex refractive index from its adjacent layers; and (2) complex refractive indices and thicknesses of the substrate and layers that correspond to a target optical spectrum $w_t(\lambda)$. The target optical spectrum $w_t(\lambda)$ is different from the theoretical optical spectrum $w_{th}(\lambda)$ associated with the characteristic, such that the difference between the target and theoretical optical spectra cause degradation of a target performance relative to a theoretical performance of the ICE within a target error tolerance. The target performance represents a finite accuracy with which an ICE having the target optical spectrum $w_t(\lambda)$ is expected to predict known values of the characteristic corresponding to a set of validation spectra of a sample with a finite (non-zero) error. Here, the predicted values of the characteristic are obtained through integration of the validation spectra of the sample respectively weighted by the ICE with the target optical spectrum $w_t(\lambda)$. The theoretical performance represents the maximum accuracy with which the ICE—if it had the theoretical optical spectrum $w_{th}(\lambda)$—would predict the known values of the characteristic corresponding to the set of validation spectra of the sample. Here, the theoretically predicted values of the characteristic would be obtained through integration of the validation spectra of the sample respectively weighted by the ICE, should the ICE have the theoretical optical spectrum $w_{th}(\lambda)$.

Figure 2:
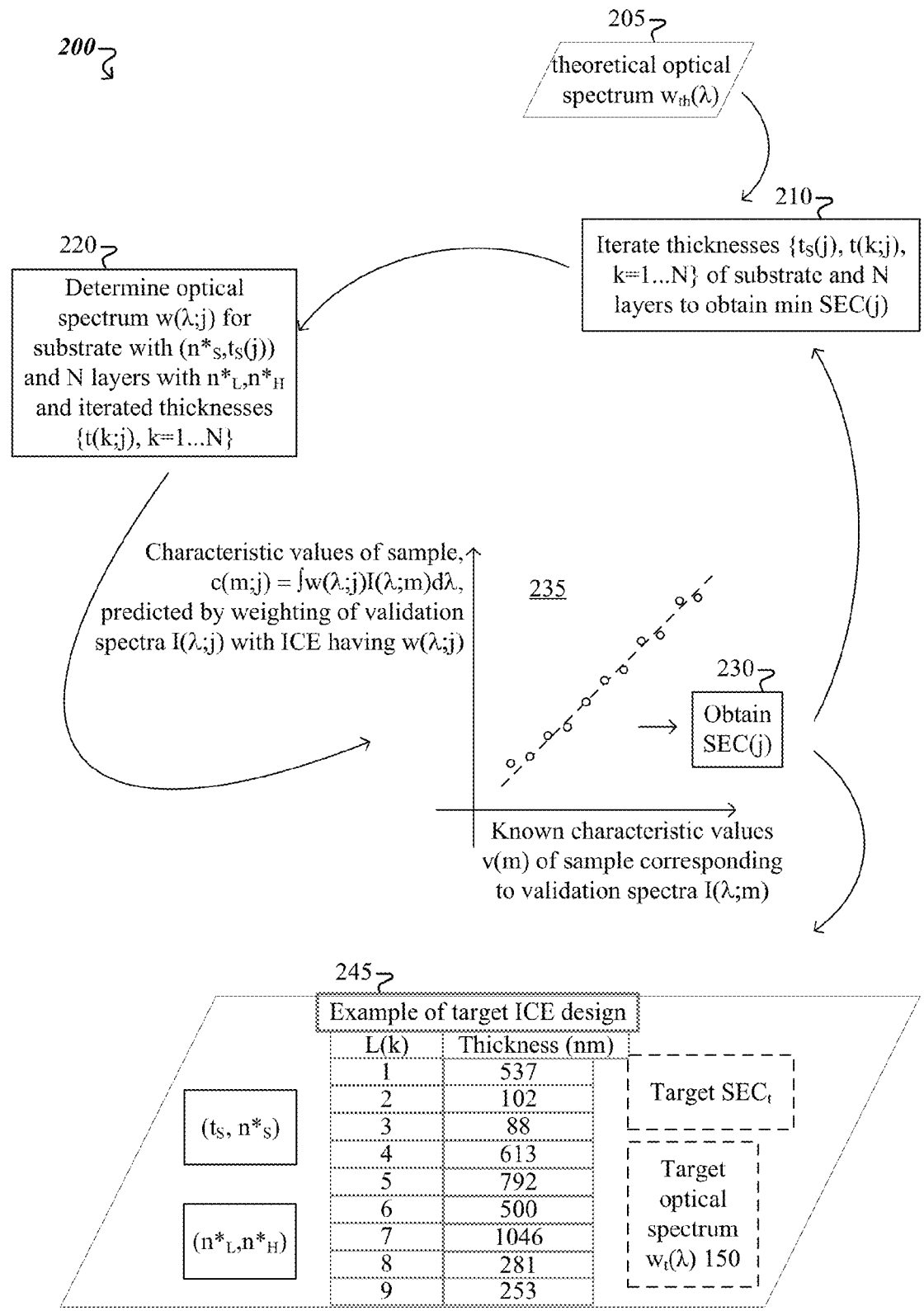
FIG. 2 is a flowchart showing an example of a process for designing an ICE.

FIG. 2 is a flow chart of an example of a process 200 for generating an ICE design. One of the inputs to the process 200 is a theoretical optical spectrum $w_{th}(\lambda)$ 205. For instance, to design an ICE for measuring concentration of a substance X in a mixture, a theoretical optical spectrum $w_{th}(\lambda)$ associated with the concentration of the substance X in the mixture, is accessed, e.g., in a data repository. As described above in this specification, the accessed theoretical optical spectrum $w_t(\lambda)$ corresponds to a spectral pattern detected offline, using a number $N_c$ of calibration spectra of the mixture, each of the $N_c$ calibration spectra corresponding to a known concentration of the substance X in the mixture. An additional input to the process 200 is a specification of materials for a substrate and ICE layers. Materials having different complex refractive indices, respectively, are specified such that adjacent ICE layers are formed from materials with different complex refractive indices. For example, a first material (e.g., Si) having a high complex refractive index $n^*_H$ and a second material (e.g., $SiO_X$) having a low complex refractive index $n^*_L$, are specified to alternately form the ICE layers. As another example, a layer can be made from high index material (e.g., Si), followed by a layer made from low index material (e.g., $SiO_X$), followed by a layer made from a different high index material (e.g., Ge), followed by a layer made from a different low index material ($MgF_2$), etc. The iterative design process 200 is performed in the following manner.

At 210 during the $j^{th}$ iteration of the design process 200, thicknesses $\{t_S(j), t(1;j), t(2;j), \ldots, t(N-1;j), t(N;j)\}$ of the substrate and a number N of layers of the ICE are iterated.

At 220, a $j^{th}$ optical spectrum $w(\lambda;j)$ of the ICE is determined corresponding to complex refractive indices and previously iterated thicknesses $\{t_X(j), t(1;j), t(21\ ;j), t(N-1;j), t(N;j)\}$ of the substrate and the N layers, each having a different complex refractive index from its adjacent layers. The iterated thicknesses of the substrate and the N layers are used to determine the corresponding $j^{th}$ optical spectrum $w(\lambda;j)$ of the ICE in accordance with conventional techniques for determining spectra of thin film interference filters.

At 230, performance of the ICE, which has the $j^{th}$ optical spectrum $w(\lambda;j)$ determined at 220, is obtained. To do so, a set of validation spectra of a sample is accessed, e.g., in a data repository. Respective values of a characteristic of the sample are known for the validation spectra. For instance, each of $N_v$ validation spectra $I(\lambda;m)$ corresponds to a value $v(m)$ of the characteristic of the sample, where $m=1, \ldots, N_v$. In the example illustrated in FIG. 2, $N_v=11$ validation spectra, respectively corresponding to 11 known values of the characteristic to be measured for the sample, are being used.

Graph 235 shows (in open circles) values c(m;j) of the characteristic of the sample predicted by integration of the validation spectra $I(\lambda;m)$ weighted with the ICE, which has the $j^{th}$ optical spectrum $w(\lambda;j)$, plotted against the known values v(m) of the characteristic of the sample corresponding to the validation spectra $I(\lambda;m)$. The predicted values c(m−;1) of the characteristic are found by substituting, in formula 165' of FIG. 1A, (1) the spectrum $I(\lambda)$ 135' of sample modified light with the respective validation spectra $I(\lambda;m)$ and (2) the target spectrum $w_t(\lambda)$ 150 with the $j^{th}$ optical spectrum $w(\lambda;j)$. In this example, performance of the ICE, which has the $j^{th}$ optical spectrum $w(\lambda;j)$, is quantified in terms of a weighted measure of distances from each of the open circles in graph 235 to the dashed-line bisector between the x and y axes. This weighted measure is referred to as the standard calibration error (SEC) of the ICE. For instance, an ICE having the theoretical spectrum $w_{th}(\lambda)$ has a theoretical $SEC_{th}$ that represents a lower bound for the SEC(j) of the ICE having the $j^{th}$ spectrum $w(\lambda;j)$ determined at 220 during the $j^{th}$ iteration of the design process 200: $SEC(j) > SEC_{th}$.

In this specification, the SEC is chosen as a metric for evaluating ICE performance for the sake of simplicity. Note that there are other figures of merit that may be used to evaluate performance of ICE, as is known in the art. For example, sensitivity—which is defined as the slope of characteristic change as a function of signal strength—can also be used to evaluate ICE performance. As another example, standard error of prediction (SEP)—which is defined in a similar manner to the SEC except it uses a different set of validation spectra—can be used to evaluate ICE performance. Any of the figure(s) of merit known in the art is/are evaluated in the same general way by comparing theoretical performance with that actually achieved. Which figure(s) of merit or combinations are used to evaluate ICE performance is determined by the specific ICE design.

The iterative design process 200 continues by iterating, at 210, the thicknesses of the substrate and the N layers. The iterating is performed such that a $(j+1)^{th}$ optical spectrum $w(\lambda;j+1)$—determined at 220 from the newly iterated thicknesses—causes, at 230, improvement in performance of the ICE, to obtain $SEC(j+1) < SEC(j)$. In some implementations, the iterative design process 200 is stopped when the ICE's performance reaches a local maximum, or equivalently, the SEC of the ICE reaches a local minimum. For example, the iterative process 200 can be stopped at the $(j+1)^{th}$ iteration when the current SEC(j+1) is larger than the last SEC(j), $SEC(j+1) > SEC(j)$. In some implementations, the iterative design process 200 is stopped when, for a given number of iterations, the ICE's performance exceeds a specified threshold performance for a given number of iterations. For example, the iterative design process 200 can be stopped at the $j^{th}$ iteration when three consecutive SEC values decrease monotonously and are less than a specified threshold value: $SEC_0 > SEC(j-2) > SEC(j-1) > SEC(j)$.

In either of these cases, an output of the iterative process 200 represents a target ICE design 245 to be used for fabricating an ICE 140, like the one described in FIG. 1A, for instance. The ICE design 245 includes specification of (1) a substrate and N layers, each having a different complex refractive index from its adjacent layers, and (2) complex refractive indices $n*_S$, $n*_H$, $n*_L$, and thicknesses $\{t_S(j), t(1;j), t(2;j), \ldots, t(N-1;j), t(N;j)\}$ of the substrate and N layers corresponding to the $j^{th}$ iteration of the process 200. Additional components of the ICE design are the optical spectrum w(—;j) and the SEC(j)—both determined during the $j^{th}$ iteration based on the thicknesses $\{t_S(j), t(1;j), t(2;j), t(N-1;j), t(N;j)\}$. As the ICE design 245 is used as input for fabrication processes described herein, the iteration index j—at which the iterative process 200 terminates—is dropped from the notations used for the components of the ICE design.

In this manner, the thicknesses of the substrate and the N layers associated with the ICE design 245 are denoted $\{t_S, t(1), t(2), t(N-1), t(N)\}$ and are referred to as the target thicknesses. The optical spectrum associated with the ICE design 245 and corresponding to the target thicknesses is referred to as the target optical spectrum $w_t(\lambda)$ 150. The SEC associated with the ICE design 245—obtained in accordance with the target optical spectrum $w_t(\lambda)$ 150 corresponding to the target thicknesses—is referred to as the target $SEC_t$. In the example illustrated in FIG. 2, the ICE design 245 has a total of N=9 alternating Si and $SiO_2$ layers, with complex refractive indices $n_{Si}$, $n_{SiO2}$, respectively. The layers' thicknesses (in nm) are shown in the table. An ICE fabricated based on the example of ICE design 245 illustrated in FIG. 2 is used to predict value(s) of concentration of substance X in wellbore fluids 130.

(3) Technologies for Fabricating ICEs Using Substrate Support Shaped to Match Spatial Profile of Deposition Plume As described above in connection with FIG. 2, an ICE design specifies a number of material layers, each having a different complex refractive index from its adjacent layers. An ICE fabricated in accordance with the ICE design has (i) a target optical spectrum $w_t(\lambda)$ and (ii) a target performance $SEC_t$, both of which correspond to the target complex refractive indices and target thicknesses of the layers specified by the ICE design. Performance of the ICE fabricated in accordance with the ICE design can be very sensitive to actual values of the complex refractive indices and thicknesses obtained during deposition. For a wide variety of reasons, the actual values of the complex refractive indices of the deposited materials and/or the rate(s) of the deposition may drift within a fabrication batch or batch-to-batch. For example, materials used for deposition (Si, $SiO_2$) may be differently contaminated, or react differently due to different chamber conditions (e.g., pressure or temperature). Further, optical (e.g., complex refractive indices) and/or physical (e.g., thicknesses) characteristics of the deposited layers may be different from their target values due to non-uniformities caused by a mismatch between the shape of a support on which substrates of the ICEs being fabricated are distributed and a spatial profile of a deposition plume provided by a deposition source. For instance, a conventional support is spaced apart from and within a field of view of a deposition source and has a flat shape. As such, if an azimuthal axis of the deposition source intersects the center of the flat support, then non-uniformities in complex refractive indices and thicknesses of the deposited layers are induced, because a distance from the deposition source to ICEs supported near the center of the support is shorter than a distance from the deposition source to the ICEs supported near the edge of the support. Thus more material is deposited per unit time at the center than at the edge.

According to the disclosed technologies, a support for supporting formed layers of ICEs is shaped and arranged relative to a deposition source used to form the layers such that a shape of the support corresponds to a spatial profile of a deposition plume provided by the deposition source. In this manner, a deposition point-source is placed at the origin of a spherically shaped support to obtain uniform characteristics of the ICE layers over the support surface. As another example, an extended (e.g., planar) deposition source that provides a deposition plume with a given spatial profile, e.g., Lambertian (cosine emission), is spaced apart from a support by a particular distance. Here, the support is prepared to have a shape that is an approximation of the given spatial profile (e.g., the Lambertian profile) at the particular distance. Many other combinations of (I) relative positions of the deposition source and the support and (II) shapes of the support relative to spatial profiles of the deposition plume are described herein. Matching the shape of the support with the spatial profile of the deposition plume leads to deposition rates and resulting optical (e.g., complex refractive indices) and physical (e.g., thicknesses) characteristics of the formed ICE layers that are uniform across the support.

By depositing layers with uniform characteristics over the support, ICE fabrication yield increases relative to conventional ICE fabrication where a shape of the flat support used during deposition is mismatched with the spatial profile of the deposition plume. Moreover, because the characteristics of the deposited layers are uniform for the ICEs distributed over the disclosed support, a number of locations of the disclosed support at which the layer characteristics are monitored can be reduced relative to conventional ICE fabrication. As such, for some support spatial profiles, monitoring layer characteristics at a single location may be sufficient to characterize the entire ICE fabrication batch. In this manner, the disclosed technologies can be used to implement ICE fabrication that can be more accurate and more efficient than conventional ICE fabrication.

Technologies are described below for fabricating ICEs using a support for supporting formed layers of ICEs, where the support is shaped and arranged relative to a deposition source used to form the layers such that a shape of the support corresponds to a spatial profile of a deposition plume provided by the deposition source. By shaping the support in this manner, material is deposited at substantially the same rate across each of the ICEs supported on the support.

Figure 3A:
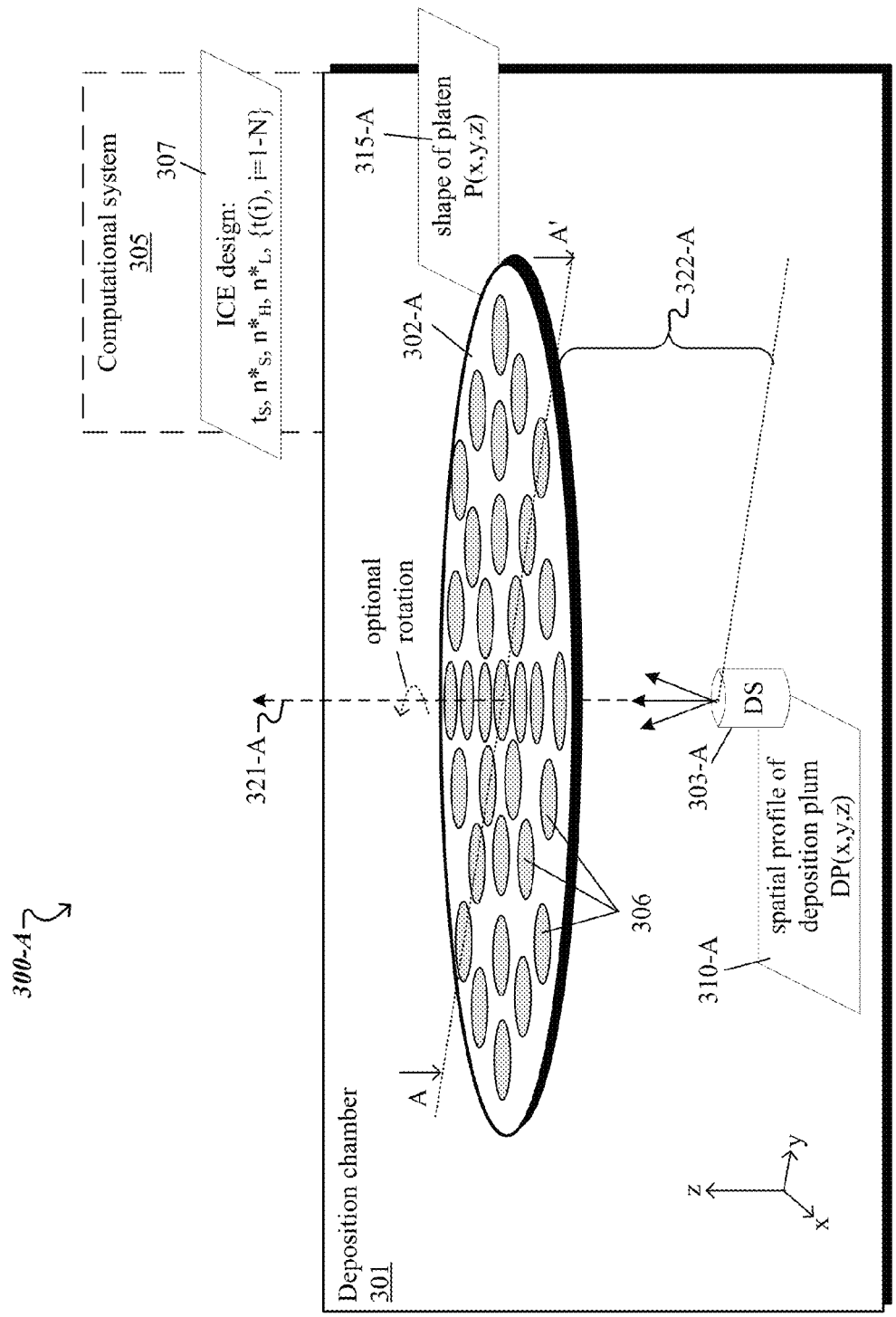
FIGS. 3A-3C show aspects of an example of a system for ICE fabrication that has a support for supporting formed layers of ICEs, where the support is shaped and arranged relative to a deposition source used to form the layers such that the shape of the support corresponds to a spatial profile of a deposition plume provided by the deposition source.
Figure 4A:
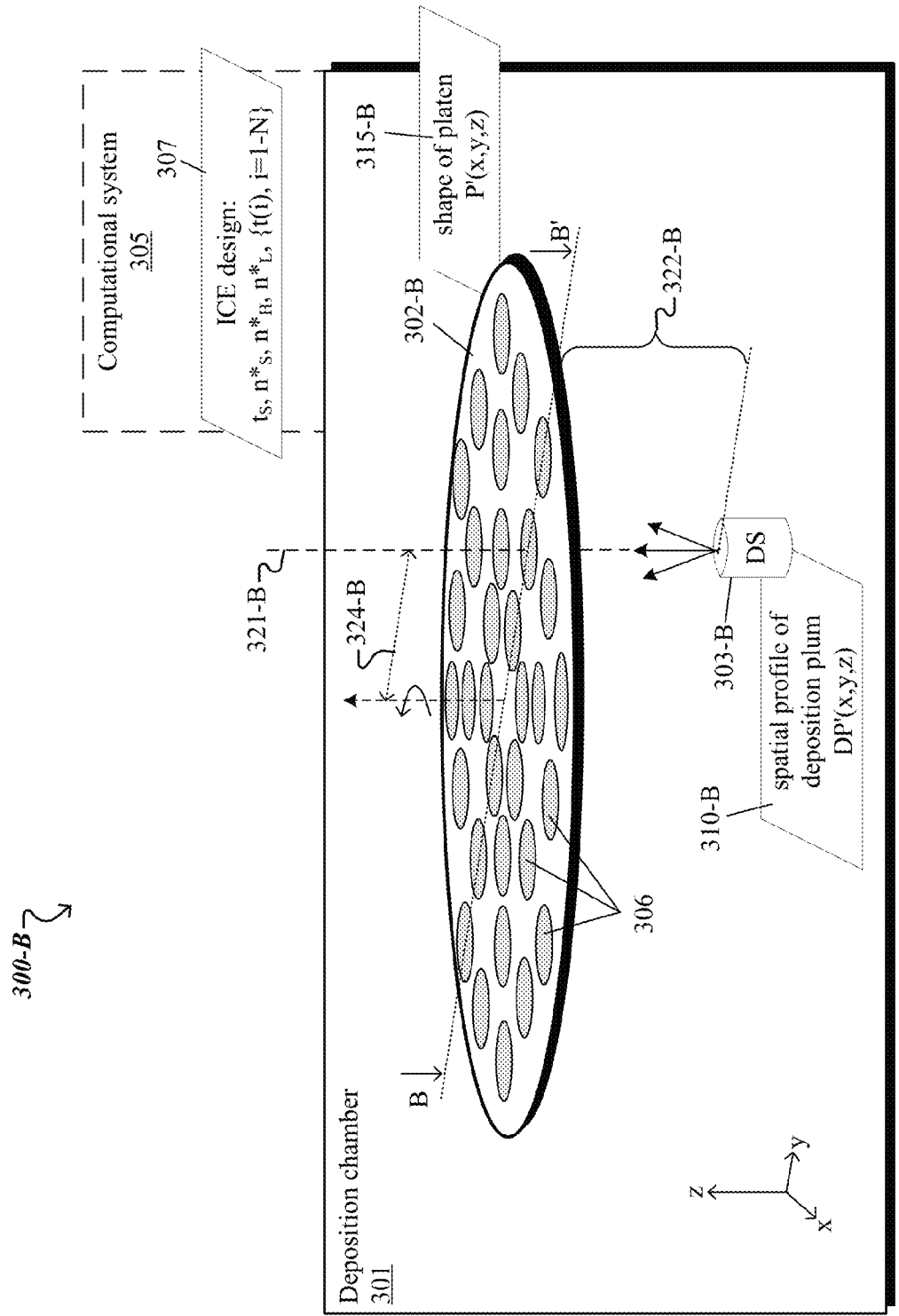
FIGS. 4A-4C show aspects of another example of a system for ICE fabrication that has another support for supporting formed layers of ICEs, where the support is shaped and arranged relative to another deposition source used to form the layers such that the shape of the other support corresponds to another spatial profile of a deposition plume provided by the other deposition source.

FIGS. 3A and 4A show implementations of an example of an ICE fabrication system 300. A target ICE design 307 can be provided to the ICE fabrication system 300 in which one or more ICEs 306 are fabricated based on the target ICE design. The ICE fabrication system 300 includes a deposition chamber 301 to fabricate one or more ICEs 306 and a computational system 305 to control the fabrication of the one or more ICEs 306 in the deposition chamber 301.

The deposition chamber 301 includes one or more deposition sources 303 to provide materials with different complex refractive indices, e.g., $n^*_L$ and $n^*_H$, used to form adjacent layers of the ICEs 306. Substrates on which layers of the ICEs 306 will be deposited are placed on a substrate support 302, such that at least some of the ICEs 306 are within the field of view of the deposition source(s) 303.

Various physical vapor deposition (PVD) techniques can be used to form a stack of layers of each of the ICEs 306 in accordance with the target ICE design 307 (corresponding to design 145 or 245, for instance.) In accordance with PVD techniques, the layers of the ICE(s) are formed by condensation of a vaporized form of material(s) of the source(s) 305, while maintaining vacuum in the deposition chamber 301. One such example of PVD technique is electron beam (E-beam) deposition, in which a beam of high energy electrons is electromagnetically focused onto material(s) of the deposition source(s) 303, e.g., either Si, or $SiO_2$, to evaporate atomic species. In some cases, E-beam deposition is assisted by ions, provided by ion-sources (not shown in FIGS. 3A and 4A), to clean or etch the ICE substrate(s); and/or to increase the energies of the evaporated material(s), such that they are deposited onto the substrates more densely, for instance. Other examples of PVD techniques that can be used to form the stack of layers of each of the ICEs 306 are cathodic arc deposition, in which an electric arc discharged at the material(s) of the deposition source(s) 303 blasts away some into ionized vapor to be deposited onto the ICEs 306 being formed; evaporative deposition, in which material(s) included in the deposition source(s) 303 is(are) heated to a high vapor pressure by electrically resistive heating; pulsed laser deposition, in which a laser ablates material(s) from the deposition source(s) 303 into a vapor; or sputter deposition, in which a glow plasma discharge (usually localized around the deposition source(s) 303 by a magnet—not shown in FIGS. 3A and 4A) bombards the material(s) of the source(s) 303 sputtering some away as a vapor for subsequent deposition.

A relative orientation of and separation between the deposition source(s) 303 and the substrate support 302 are configured to provide desired deposition rate(s) and spatial uniformity across the ICEs 306 disposed on the substrate support 302. With reference to FIG. 3A, the implementation of the ICE fabrication system 300-A includes a substrate support 302-A that is spaced apart from the deposition source 303-A by a separation 322-A along an azimuthal axis 321-A of the deposition source 303-A. Here, the deposition source 303-A provides a deposition plume with a spatial profile 310-A. The spatial profile 310-A of the deposition plume can be expressed as $$DP(x, y, z) = \sum_{j=1}^{N} d(j) A(j; x, y, z). \quad (1)$$

In equation (1), the spatial profile 310-A of the deposition plume is expressed in Cartesian coordinates (x,y,z) as an expansion of base functions $\Delta(j;x,y,z)$, each of the base functions having a respective contribution given in terms of an associated coefficient d(j), j=1–N. Here, the z-axis of the Cartesian coordinates coincides with the azimuthal axis 321-A of the deposition source 303-A. Examples of base functions A(x,y,z) used in equation (1) are Zernike polynomials, Hermite polynomials, etc. An infinite number of terms are used in the expansion of DP(x,y,z) to exactly express the spatial profile 310-A of the deposition plume. A smaller number of terms, e.g., 7, can be used in the expansion of DP(x,y,z) to approximate the spatial profile 310-A of the deposition plume. In the latter case, at least some of the coefficients d(j), for j=1-7, are different from zero and the remaining coefficients d(j) are zero: d(j)=0, for j≥8.

In some cases, the plume spatial profile 310-A has the same spatial symmetry relative to both x and y axes. For example, the spatial profile 310-A of the deposition plume provided by a point-like deposition source 310-A is approximately a sphere. As another example, the spatial profile 310-A of the deposition plume provided by an extended source has a Lambertian (cosine emission) distribution. In either of the foregoing examples, the expansion of DP(x,y,z) in equation (1) can be rewritten as an expansion in cylindrical coordinates DP(z, r) without terms that depend from the angular coordinate θ. Other examples of spatial profiles 310-A of the deposition plume are a parabolic profile or a hyperbolic profile, for instance. In other cases, the plume spatial profile 310-A has a first symmetry (e.g., spherical) relative to the x-axis and a second, different symmetry (e.g., Lambertian) relative to the y-axis. In some other cases, the plume spatial profile 310-A is symmetric relative to the x-axis and is asymmetric relative to the y-axis. In yet some other cases, the plume spatial profile 310-A is asymmetric relative to both x and y axes.

Here, a combination of (I) the separation 322-A between the substrate support 302-A and the deposition source 303-A and (II) the spatial profile 310-A of the deposition plume is selected such that all the substrates of the ICEs 306 distributed on the substrate support 302-A are within the field of view of the deposition source 303-A.

In this example, the substrate support 302-A has a shape 315-A. The shape 315-A of the substrate support 302-A can be expressed as $$P(x, y, z) = \sum_{j=1}^{N} s(j) A(j; x, y, z). \quad (2)$$

In equation (2), the shape 315-A of the substrate support 302-A is expressed in the Cartesian coordinates (x,y,z) as an expansion of the same base functions $A(j;x,y,z)$ used in the expansion of the spatial profile 310-A of the deposition plume. Here, each of the base functions has a respective contribution given in terms of an associated coefficient s(j), j=1–N. The shape 315-A of the substrate support 302-A is said to match the spatial profile 310-A of the deposition plume when a difference surface $D(j;x,y,z)$ is substantially flat. For example, the difference surface $D(j;x,y,z)$ is said to be flat when the following inequality holds true:

$$\varepsilon_1 \geq \sum_{j=1}^{N} |d(j) - s(j)|. \quad (3)$$

In equation (3), the threshold $\varepsilon_1$ is predefined. As another example, the difference surface $D(j;x,y,z)$ is said to be flat when the following inequality holds true:

$$\varepsilon_2 \geq \sum_{j=1}^{N} (d(j) - s(j))^2. \quad (4)$$

In equation (4), the threshold $\varepsilon_2$ is predefined. In some implementations, the threshold $\varepsilon_1$ or $\varepsilon_2$ is predefined such that a deposition rate varies by less than 0.1% (or in some cases 0.01% or 0.001%) across the ICEs 306 supported by the support 302-A. In some implementations, the threshold $\varepsilon_1$ or $\varepsilon_2$ is predefined such that performance of ICEs 306 that were supported by the support 302-A during fabrication varies by less than 10% (or in some case 5% or 1%). For example, the shape 315-A of the substrate support 302-A matches the spatial profile 310-A of the deposition plume such that $\Delta SEC/SEC_t \leq 10\%$ over the ICEs 306 supported by the support 302-A during fabrication. Here, $SEC_t$ is used to quantify a target accuracy associated with the ICE design 307, and $\Delta SEC$ represents variation of the accuracy of ICEs fabricated during a single fabrication batch. Other metrics of the ICE performance, such as e.g., sensitivity, can be used to predefine the threshold $\varepsilon_1$ or $\varepsilon_2$ for matching the shape 315-A of the substrate support 302-A to the spatial profile 310-A of the deposition plume.

Once the spatial profile 310-A of the deposition plume is known, a first surface of the substrate support 302 on which the substrates of the ICEs 306 are to be supported can be prepared (e.g., polished, then lapped) to have a shape 315-A that matches the known spatial profile 310-A of the deposition plume, based either on equation (3) or (4). In some implementations, the plume spatial profile 310-A is a spherical profile with a particular radius. In this case the first surface of the substrate support 302-A is prepared as a portion of a sphere having the particular radius and is placed at separation distance 322-A equal to the particular radius from the deposition source. In other implementations, the plume spatial profile 310-A is a Lambertian (cosine emission) profile, so the first surface of the substrate support 302-A is shaped to be an approximation of the Lambertian profile at the separation distance 322-A. In some other implementations, the plume spatial profile 310-A is a parabolic profile with particular foci. In this case, the first surface of the substrate support 302-A is prepared as a portion of a paraboloid having the particular foci and is placed at separation distance 322-A from the deposition source corresponding to the nearest of the foci. In yet some other implementations, the plume spatial profile 310-A is a hyperbolic profile with particular foci. In this case, the first surface of the substrate support 302-A is prepared as a portion of a hyperboloid having the particular foci and is placed at separation distance 322-A from the deposition source corresponding to the nearest of the foci.

Figure 3B:
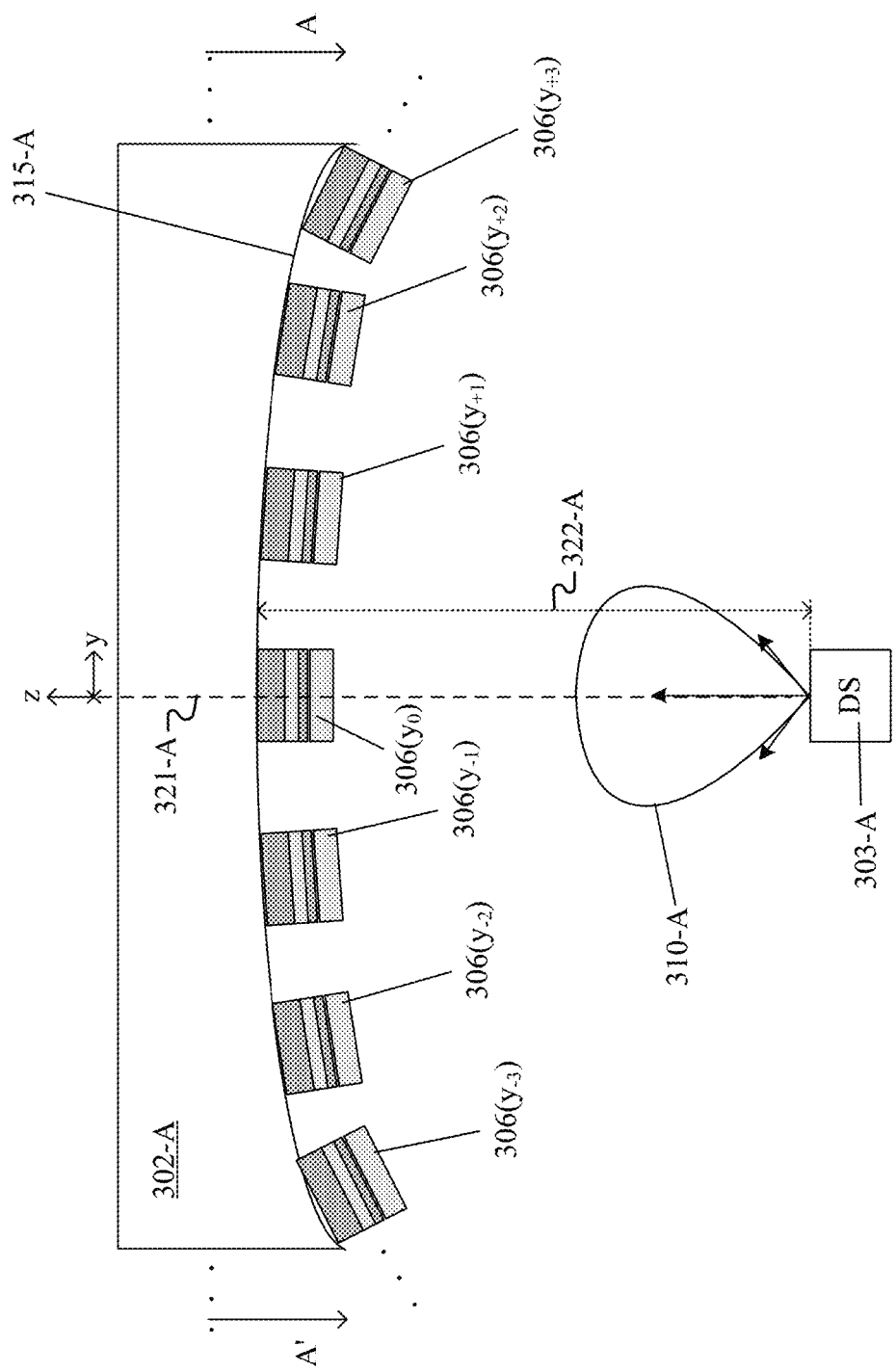

In some cases, the prepared first surface of the substrate support 302-A has a shape 315-A with continuous slope (derivative). FIG. 3B shows several ICEs 306 distributed along a cross-section AA' of the prepared first surface of the substrate support 302-A having a shape 315-A with continuous slope and being separated from the deposition source 303-A by a separation 322-A. The shape 315-A with continuous slope is selected to match, in accordance with equations (3) or (4), the spatial profile of the deposition source 303-A along the cross-section AA'. An ICE $306(y_0)$ is disposed at a lateral distance $y_0=0$ from the azimuthal axis 321-A of the deposition source 303-A; two ICEs $306(y_{+1})$ and $306(y_{-1})$ are disposed at a lateral distance $|y_{+1}|$ from the azimuthal axis 321-A at locations $y_{+1}$ and $y_{-1}$; two ICEs $306(y_{+2})$ and $306(y_{-2})$ are disposed at another lateral distance $|y_{\pm2}|$ from the azimuthal axis 321-A at locations $y_{+2}$ and $y_{-2}$; and two ICEs $306(y_{+3})$ and $306(y_{-3})$ are disposed at yet another lateral distance $|y_{+3}|$ from the azimuthal axis 321-A at locations $y_{+3}$ and $y_{-3}$.

Figure 3C:
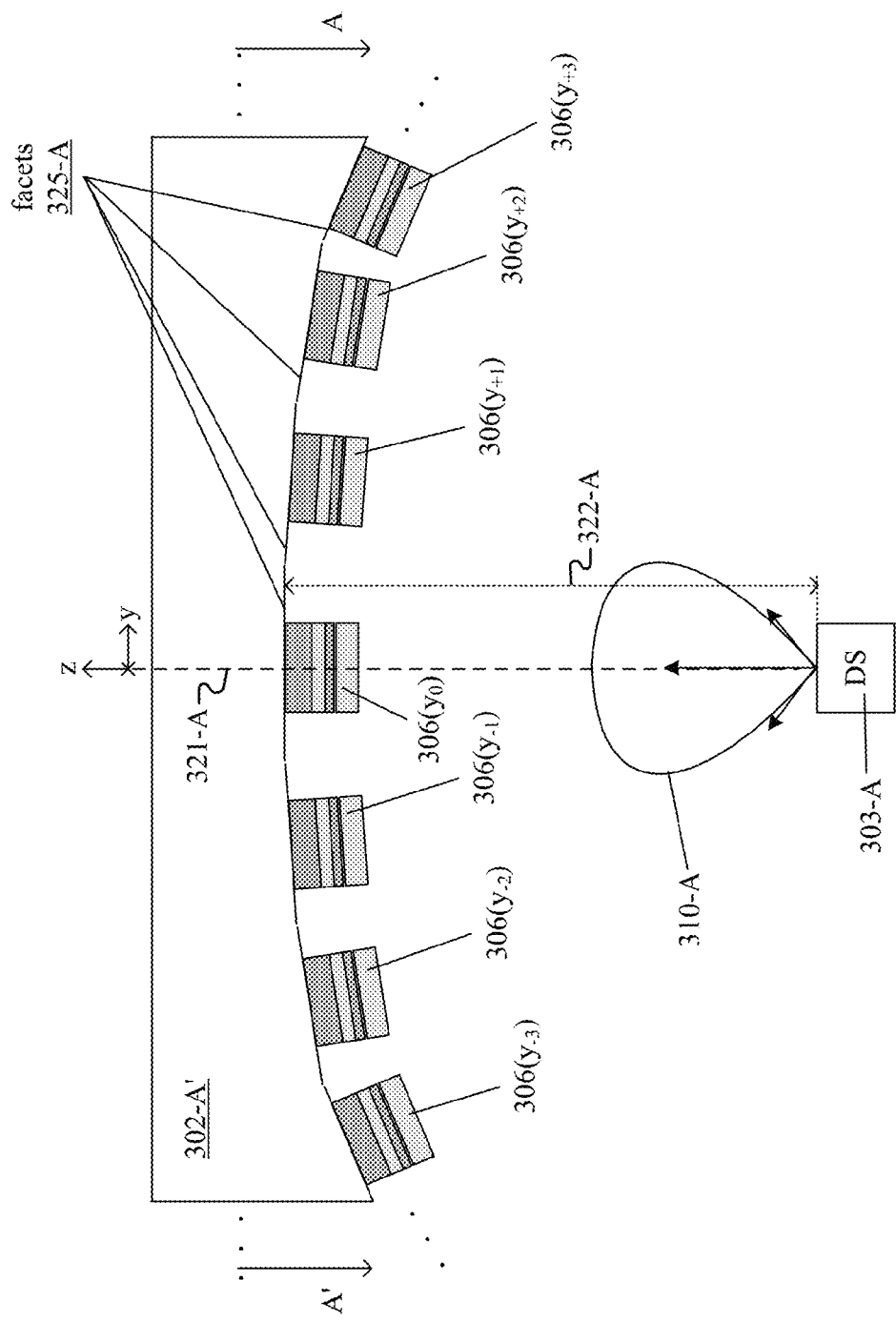

In other cases, the prepared first surface of the substrate support 302-A' has a shape which includes multiple facets (or equivalently has a discontinuous slope). FIG. 3C shows several ICEs 306 distributed along a cross-section AA' of the prepared first surface of the substrate support 302-A' having a shape which includes multiple facets 325-A and being separated from the deposition source 303-A by a separation 322-A. Relative sizes and orientations of the multiple facets 325-A are selected such that an envelope of the multiple facets 325-A matches, in accordance with equations (3) or (4), the spatial profile of the deposition source 303-A along the cross-section AA'. An ICE $306(y_0)$ is disposed on a facet centered at a lateral distance $y_0=0$ from the azimuthal axis 321-A; two ICEs $306(y_{+1})$ and $306(y_{-1})$ are disposed on respective facets centered at a lateral distance $|y_{+1}|$ from the azimuthal axis 321-A at respective locations $y_{+1}$ and $y_{-1}$; two ICEs $306(y_{+2})$ and $306(y_{-2})$ are disposed on other respective facets centered at a different lateral distance $|y_{\pm2}|$ from the azimuthal axis 321-A at respective locations $y_{+2}$ and $y_{-2}$; and two ICEs $306(y_{+3})$ and $306(y_{-3})$ are disposed on yet other respective facets centered at a different lateral distance $|y_{\pm3}|$ from the azimuthal axis 321-A at locations $y_{+3}$ and $y_{-3}$.

In this manner, deposition rate is constant over the first surface of the substrate support 302-A/302-A' prepared to have the shape 315-A or the multiple facets 325-A, and, hence, optical (e.g., complex refractive indices) and physical (e.g., thicknesses) characteristics of the deposited layers of the ICEs 306($y±_j$), j=0-3, are uniform across the ICEs supported on the substrate support 302-A/302-A'.

In some implementations, the plume spatial profile 310-A is known only along a first direction, e.g., along the cross-section AA' in the plane of FIG. 3B or 3C, but it is unknown in other directions, e.g., along a direction orthogonal to the plane of FIG. 3B or 3C. Here, the substrate support 302-A/302-A' is moved with respect to the azimuthal axis 321-A, such that a direction of motion is orthogonal to the first direction, e.g., the direction of motion is orthogonal on the cross-section AA' in the plane of FIG. 3B or 3C. In some cases, the substrate support 302-A/302-A' is moved along the direction of motion in a periodic manner with respect to the azimuthal axis 321-A. In addition, the first surface of the substrate support 302-A/302-A' that supports the ICEs 306 is prepared such that its spatial profile 315-A/325-A matches (in accordance with equations 3 or 4), in a cross-section AA' along a first direction orthogonal to the direction of motion, the plume spatial profile 310-A.

In some cases, the direction motion is orthogonal on and intersects an azimuthal axis 321-A of the plume spatial profile 310-A, and the first surface of the support shape 315-A/325-A, at least in the cross-section AA' along the first direction, is centered on the azimuthal axis 321-A of the plume spatial profile 310-A. In the case illustrated in FIG. 3B, the substrate support 302-A is a (smooth) cylindrical plate with a longitudinal axis parallel with the direction of motion along which the cylindrical plate is translated relative to the azimuthal axis 321-A of the plume spatial profile 310-A. In the case illustrated in FIG. 3C, the substrate support 302-A' is a (faceted) prismatic plate with a longitudinal axis parallel with the direction of motion along which the prismatic plate is translated relative to the azimuthal axis 321-A of the plume spatial profile 310-A.

In some cases shown in FIG. 3A, a center axis of the substrate support 302-A spatial profile is common with an azimuthal axis 321-A of the plume spatial profile 310-A. In these cases, the substrate support 302-A is a circular plate and the circular plate is rotated (along angular direction θ) around its center axis which is common with the azimuthal axis 321-A of the plume spatial profile 310-A.

Whether in the case of the cylindrical or prismatic plate translated along the direction of motion orthogonal on the cross-section AA', or the circular plate rotated about the azimuthal axis 321-A of the deposition plume 310-A, the first surface of the substrate support 302-A/302-A' that supports the ICEs 306 is prepared such that its shape 315-A/325-A matches (in accordance with equations 3 or 4), in the cross-section AA' along a first direction orthogonal to the direction of motion, the plume spatial profile 310-A. In some implementations, the plume spatial profile 310-A is a Lambertian (cosine emission) profile of an extended source, and the shape 315-A/325-A of the substrate support 302-A/302-A', in the cross-section AA' along the first direction, is an approximation of the Lambertian profile. In other implementations, the plume spatial profile 310-A is a spherical profile of a point source, and the shape 315-A/325-A of the first surface of the substrate support 302-A/302-A', in the cross-section AA' along the first direction, is an approximation of the spherical profile. In some other implementations, the plume spatial profile 310-A is a parabolic profile, and the shape 315-A/325-A of the first surface of the substrate support 302-A/302-A', in the cross-section AA' along the first direction, is an approximation of the parabolic profile. In yet other implementations, the plume spatial profile 310-A is a hyperbolic profile, and the shape 315-A/325-A of the first surface of the substrate support 302-A/302-A', in the cross-section AA' along the first direction, is an approximation of the hyperbolic profile.

With reference to FIG. 4A, the implementation of the ICE fabrication system 300-B includes a circular substrate support 302-B (also referred to as platen) that is spaced apart from the deposition source 303-B by a separation 322-B along an azimuthal axis 321-B of the deposition source 303-A. The center of the circular substrate support 302-B has a center shifted to a lateral separation 324-B from the azimuthal axis 321-B. For example, a diameter of such substrate support 302-B is 13" (or about 330 mm) and its center is placed a distance of 6.5" (or about 165 mm) from the azimuthal axis 321-B. If an ICE diameter is 1" (or about 25 mm), up to 66 ICEs 306 can be placed on the substrate support 302-B in the configuration illustrated in FIG. 4A.

In this example, the deposition source 303-B provides a deposition plume with a spatial profile 310-B. The spatial profile 310-B of the deposition plume can be expressed as $$DP'(x, y, z) = \sum_{j=1}^{N} d'(j)A(j; x, y, z). \qquad (1')$$

In equation (1'), the spatial profile 310-B of the deposition plume is expressed in Cartesian coordinates (x,y,z) as an expansion of the same base functions Δ(j;x,y,z) from equations (1) and (2), each of the base functions having a respective contribution given in terms of an associated coefficient d'(j), j=1–N. Here, the z-axis of the Cartesian coordinates coincides with the azimuthal axis 321-B of the deposition source 303-B.

A combination of (I) the separation 322-B along the azimuthal axis 321-B between the circular substrate support 302-B and the deposition source 303-B, (II) the lateral separation 324-B from the center of the circular substrate support 302-B to the azimuthal axis 321-B and (III) the spatial profile 310-B of the deposition plume is selected such that the field of view of the deposition source 303-B spans a length equal to about a radius (or half the diameter) of the circular substrate support 302-B. Here, the circular substrate support 302-B is rotated about its center axis during deposition of layers of the ICEs 306. Additionally in this example, the center axis of the circular substrate support 302-B is parallel to the azimuthal axis 321-B of the deposition source 303-B and displaced relative to the azimuthal axis 321-B by half the radius of the circular substrate support 302-B.

In this manner, a first surface of the circular substrate support 302-B on which the substrates of the ICEs 306 are to be supported can be prepared (e.g., polished, then lapped) to have a shape 315-B that matches the spatial profile 310-B of the deposition plume along the radial direction of the circular substrate support 302-B. The shape 315-B of the circular substrate support 302-B can be expressed as:

$$P'(x, y, z) = \sum_{j=1}^{N} s'(j)A(j; x, y, z). \qquad (2')$$

In equation (2'), the shape 315-B of the circular substrate support 302-B is expressed in the Cartesian coordinates (x,y, z) as an expansion of the same base functions Δ(j;x,y,z) used in the expansion of the spatial profile 310-B of the deposition plume. Here, each of the base functions has a respective contribution given in terms of an associated coefficient s'(j), j=1–N. In this example, the shape 315-B of the circular substrate support 302-B is said to match the spatial profile 310-B of the deposition plume along a radial direction of the circular substrate support 302-B when a difference cross-section Δ(j; y,z) along the radial direction is substantially a straight line. For example, the difference cross-section Δ(j;y,z) along the radial direction is said to be a straight line when the following inequality holds true:

$$\varepsilon_1' \geq \sum_{j=1}^{N} |d'(j) - s'(j)|. \quad (3')$$

In equation (3'), the threshold $\in'_1$ is predefined. As another example, the difference cross-section Δ(j;y,z) along the radial direction is said to be a straight line when the following inequality holds true:

$$\varepsilon_2' \geq \sum_{j=1}^{N} (d'(j) - s'(j))^2. \quad (4')$$

In equation (4'), the threshold $\in'_2$ is predefined. In this manner, the first surface of the circular substrate support 302-B is prepared to have a shape 315-B that matches a known spatial profile 310-B of the deposition plume along a radial direction of the circular substrate support 302-B, based on either equation (3') or (4'). Once again, the threshold $\in'_1$ or $\in'_2$ is predefined such that a deposition rate varies by less than a 0.1% (or in some cases 0.01% or 0.001%) across the ICEs 306 supported by the support 302-B. In some implementations, the threshold $\in'_1$ or $\in'_2$ is predefined such that performance of ICEs 306 that were supported by the support 302-B during fabrication varies by less than 10% (or in some case 5% or 1%). For example, the shape 315-B of the substrate support 302-B along its radial direction matches the spatial profile 310-B of the deposition plume such that ΔSEC/SEC$_i$≤10% over the ICEs 306 supported by the support 302-B during fabrication.

In some implementations, the plume spatial profile 310-B is a spherical profile with a particular radius. In this case, the first surface of the circular substrate support 302-B has a shape 315-B along the radial direction that is an approximation of the spherical profile and is disposed relative to the deposition source 303-B at a separation distance 322-B along the azimuthal axis 321-B equal to the particular radius, such that the azimuthal axis 321-B intersects the first surface at a lateral distance 324-B—relative the center of the circular substrate support 302-B—equal to half the radius of the circular substrate support 302-B.

In other implementations, the plume spatial profile 310-B is a Lambertian (cosine emission) profile, so the first surface of the circular substrate support 302-B has a shape 315-B along the radical direction that is an approximation of the Lambertian profile at the separation distance 322-B B along the azimuthal axis 321-B from the deposition source 303-B, such that the azimuthal axis 321-B intersects the first surface at a lateral distance 324-B—relative the center of the circular substrate support 302-B—equal to half the radius of the circular substrate support 302-B.

In some other implementations, the plume spatial profile 310-B is a parabolic profile with particular foci. In this case, the first surface of the circular substrate support 302-B has a shape 315-B along the radial direction that is an approximation of the parabolic profile and is disposed relative to the deposition source 303-B at a separation distance 322-B along the azimuthal axis 321-B equal to a distance to the nearest foci, such that the azimuthal axis 321-B intersects the first surface at a lateral distance 324-B—relative the center of the circular substrate support 302-B—equal to half the radius of the circular substrate support 302-B.

In yet some other implementations, the plume spatial profile 310-B is a hyperbolic profile with particular foci. In this case, the first surface of the circular substrate support 302-B has a shape 315-B along the radial direction that is an approximation of the hyperbolic profile and is disposed relative to the deposition source 303-B at a separation distance 322-B along the azimuthal axis 321-B equal to a distance to the nearest foci, such that the azimuthal axis 321-B intersects the first surface at a lateral distance 324-B—relative the center of the circular substrate support 302-B—equal to half the radius of the circular substrate support 302-B.

Figure 4B:
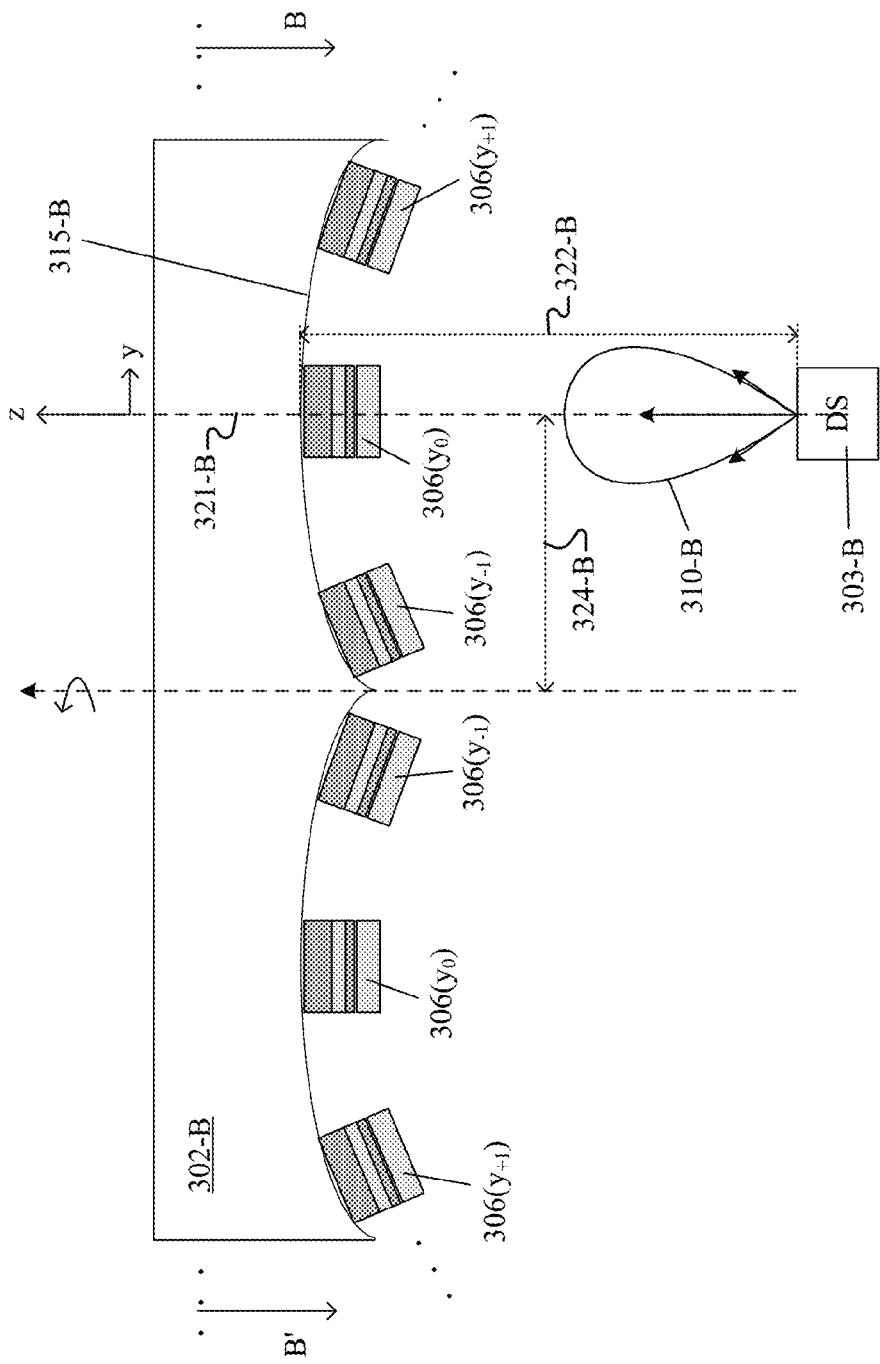

In some cases, the first surface of the circular substrate support 302-B has a shape 315-B with continuous slope (derivative) along a radial direction from the center to the edge of the circular substrate support 302-B. FIG. 4B shows several ICEs 306 distributed along a diameter BB' of the first surface of the circular substrate support 302-B having a shape 315-B with continuous slope. The shape 315-B with continuous slope is selected to match, in accordance with equations (3') or (4'), the spatial profile of the deposition source 303-B along a radius of the diameter BB'. Here, the circular substrate support 302-B rotates around its center axis that is displaced relative to the azimuthal axis 321-B by a lateral separation 324-B equal to half the radius of the circular substrate support 302-B and is separated from the deposition source 303-B by a separation 322-B along the azimuthal axis 321-B. ICEs 306($y_0$) disposed at a first radial distance from the center of the circular substrate support 302-B rotate through the field of view of the deposition source 303-B at a lateral distance $y_0$=0 from the azimuthal axis 321-B; ICEs 306($y_{+1}$) disposed at a second radial distance and ICEs 306($y_{-1}$) disposed at a third lateral radial distance rotate through the field of view of the deposition source 303-B at another lateral distance $|y_{\pm 1}|$ from the azimuthal axis 321-B.

Figure 4C:
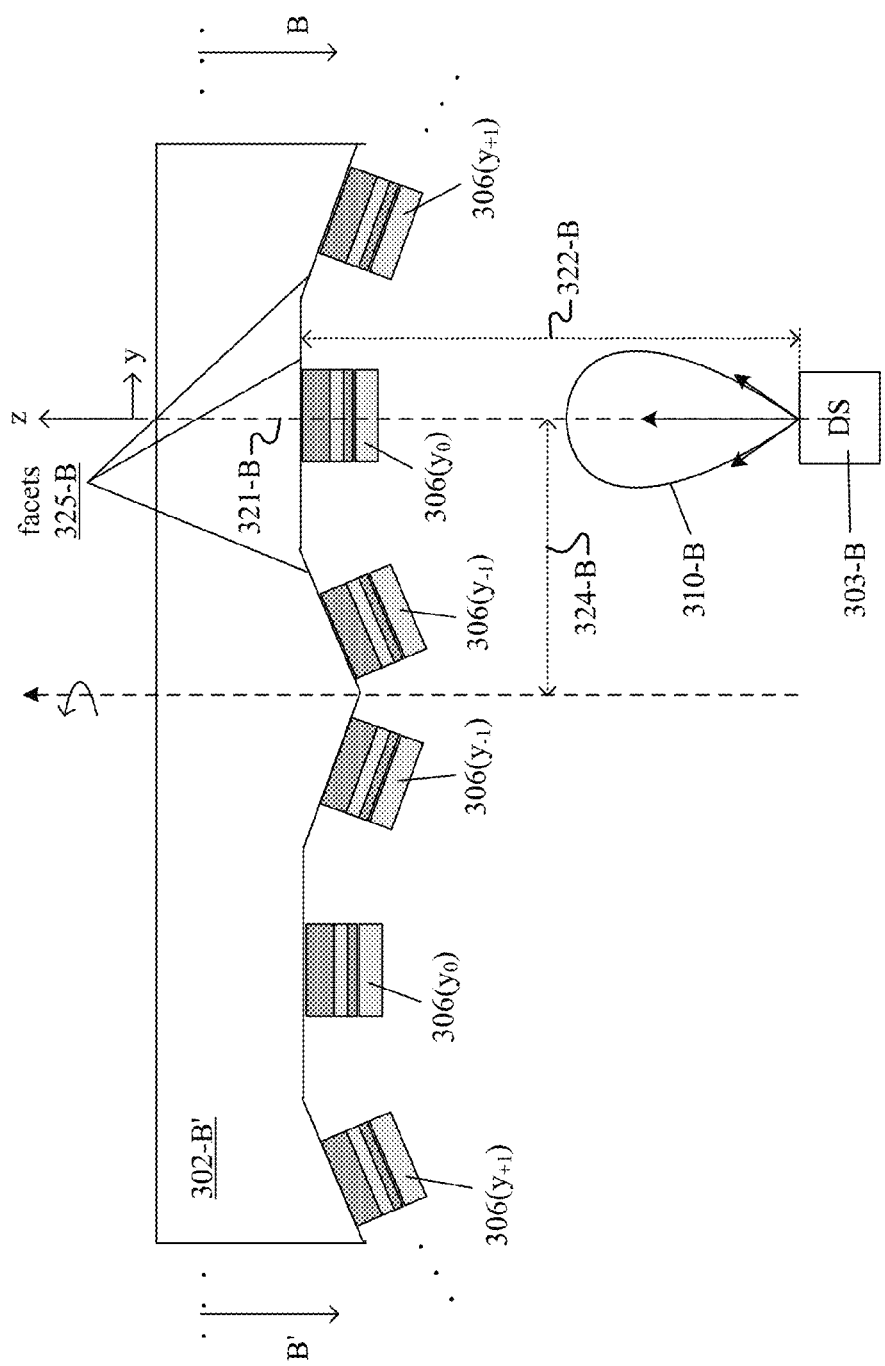

In other cases, the first surface of the circular substrate support 302-B has a shape which includes multiple radial facets (or equivalently has a discontinuous slope) along a radial direction from the center to the edge of the circular substrate support 302-B'. FIG. 4C shows several ICEs 306 distributed along a diameter BB' of the first surface of the circular substrate support 302-B' having a shape which includes multiple radial facets 325-B. Relative sizes and orientations of the multiple radial facets 325-B are selected such that an envelope of the multiple radial facets 325-B matches, in accordance with equations (3') or (4'), the spatial profile of the deposition source 303-B along a radius of the diameter BB'. Here, the circular substrate support 302-B' rotates around its center axis that is displaced relative to the azimuthal axis 321-B by a lateral separation 324-B equal to half the radius of the circular substrate support 302-B' and is separated from the deposition source 303-B by a separation 322-B along the azimuthal axis 321-B. ICEs 306($y_0$) disposed on a first radial facet centered at a first radial distance from the center of the circular substrate support 302-B' rotate through the field of view of the deposition source 303-B at a lateral distance $y_0=0$ from the azimuthal axis 321-B; ICEs 306($y_{+1}$) disposed on a second radial facet centered at a second radial distance and ICEs 306($y_{-1}$) disposed on a third radial facet centered at a third lateral radial distance rotate through the field of view of the deposition source 303-B at another lateral distance $|y_{\pm 1}|$ from the azimuthal axis 321-B.

In this manner, a deposition rate, R, is constant over the first surface of the substrate support 302-B/302-B' prepared to have the shape 315-B or the multiple radial facets 325-B, and, hence, optical (e.g., complex refractive indices) and physical (e.g., thicknesses) characteristics of the deposited layers of the ICEs 306($y_{\pm j}$) j=0-1, are uniform across the ICEs supported on the substrate support 302-B/302-B'.

A physical thickness monitor, e.g., a quartz crystal microbalance (not shown in FIGS. 3A and 4A), is used to measure the constant deposition rate R. The measured deposition rate R is used to control power provided to the deposition source(s) 303. For instance, if an ICE design specifies that a $j^{th}$ layer L(j) of the N layers of an ICE is a Si layer with a target thickness t(j), a stack including (j−1) previously formed ICE layers is exposed to a Si source—from among the deposition sources 303—for a duration $\Delta T(j)=t(j)/R_{Si}$, where the $R_{Si}$ is the measured deposition rate of the Si source.

Actual values of complex refractive indices and thickness of the deposited layers L(1), . . . , L(j−1), L(j) are determined from measurements of characteristics of probe-light that interacted with the formed layers. Note that probe-light represents any type of electromagnetic radiation having one or more probe wavelengths from an appropriate region of the electromagnetic spectrum. For instance, such characteristics of the interacted probe-light are measured using one or more of ellipsometry, optical monitoring, or spectroscopy (not shown in FIG. 3A or 4A.) As the shape 315A/B of the substrate supports 302-A/B or the envelope of the multiple facets 325A/B or 302-A'/B' of the substrate supports 302-A'/B' match the spatial profiles of the deposition sources 303-A/B—least along a cross-section AA' or BB' orthogonal to the direction of motion of the substrate supports—deposition rates and the resulting optical (e.g., complex refractive indices) and physical (e.g., thicknesses) characteristics of the formed ICE layers are the same everywhere on (at all locations of) the substrate supports 302-A/B or 302-A'/B'. Because the characteristics of the deposited layers are uniform for the ICEs 306 distributed over the substrate supports 302-A/B or 302-A'/B', a number of locations of the substrate supports 302-A/B or 302-A'/B' at which the layer characteristics are monitored can be reduced relative to conventional ICE fabrication. In some cases, the layer characteristics monitored at a single location of the substrate supports 302-A/B or 302-A'/B' may be sufficient to characterize the entire batch of ICEs 306. This single monitoring location can be at a lateral distance $y_0=0$ relative to the azimuthal axis 321-A/B of the deposition source 303-A/B, for instance.

In this manner, the substrate supports 302-A/B having shapes 315-A/B (or the substrate supports 302-A'/B' having envelopes of multiple facets 325-A/B) that are matched with spatial profiles 310-A/B of deposition plums can be used in ICE fabrication systems 300-A/B to fabricate ICEs more accurately and more efficiently relative to conventional ICE fabrication which uses flat substrate supports that are mismatched with the spatial profiles of deposition plums.

The computational system 305 includes one or more hardware processors and memory. The memory encodes instructions that, when executed by the one or more hardware processors, cause the fabrication system 300 to perform processes for fabricating the ICEs 306. The computational system 305 also includes or is communicatively coupled with a storage system that stores one or more ICE designs 307, aspects of the deposition capability, and other information. The stored ICE designs can be organized in design libraries by a variety of criteria, such as ICE designs used to fabricate ICEs for determining values of a particular characteristic over many substances (e.g. the GOR ratio in crude oil, refined hydrocarbons, mud, etc.), or ICE designs used to fabricate ICEs for determining values of many characteristics of a given substance (e.g., viscosity, GOR, density, etc., of crude oil.) In this manner, upon receipt of an instruction to fabricate an ICE for measuring a given characteristic of a substance, the computational system 305 accesses such a design library and retrieves an appropriate ICE design 307 that is associated with the given characteristic of the substance.

The retrieved ICE design 307 includes specification of a substrate and a total number N of layers to be formed in the deposition chamber 301 on the substrate; specification of a complex refractive index $n^*_S$ of a material of the substrate, a high complex refractive index $n^*_H$ and a low complex refractive index $n^*_L$ of materials (e.g., Si and SiO$_2$) to form the N layers with adjacent layers having different complex refractive indices; and specification of target thicknesses $\{t_S, t(k), k=1-N\}$ of the substrate and the N layers. Implicitly or explicitly, the ICE design 307 also can include specification of a target optical spectrum $w_t(\lambda)$ associated with the given characteristic; and specification of a target SEC$_t$ representing expected performance of an ICE associated with the retrieved ICE design 307. The foregoing items of the retrieved ICE design 307 were determined, prior to fabricating the ICEs 306, in accordance with the ICE design process 200 described above in connection with FIG. 2. In some implementations, the ICE design 307 can include indication of maximum allowed SEC$_{max}$ caused by fabrication errors. Figures of merit other than the target SEC$_t$ can be included in the retrieved ICE design 307, e.g., SEP, the ICE sensitivity, etc.

The complex refractive indices and target thicknesses $\{t(k), k=1-N\}$ of the N layers, as specified by the retrieved ICE design 307, are used by the computational system 305, in conjunction with aspects of deposition capability of the ICE fab system 300, to control deposition rate(s) of the deposition source(s) 303 and respective deposition times for forming the ICE layers. While forming the ICE layers, the computational system 305 instructs a measurement system associated with the ICE fabrication system 300 to measure characteristics of probe-light that interacted with formed layers of the ICE by performing at one or more in-situ measurements. The measured characteristics of the probe-light that interacted with the formed layers of the ICE are used by the computational system 305 to determine complex refractive indices and thicknesses of the formed layers of the ICE. If necessary, the computational system 305 then instructs the ICE fabrication system 300 to adjust the forming of layers remaining to be formed based on the determined complex refractive indices and thicknesses of the formed layers of the ICE.

Some embodiments have been described in detail above, and various modifications are possible. While this specification contains many specifics, these should not be construed as limitations on the scope of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination.

Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments.

Other embodiments fall within the scope of the following claims.

What is claimed is:

1. A system comprising:
a computational system to receive a design of an integrated computational element (ICE), the ICE design comprising specification of a substrate and a plurality of layers, their respective target thicknesses and complex refractive indices; and
a deposition chamber comprising
a deposition source to provide a deposition plume having a plume spatial profile, and
a support to support a plurality of instances of the substrate during fabrication of a plurality of instances of an ICE in accordance with the ICE design, wherein the support
is spaced apart from the deposition source along an azimuthal axis of the plume spatial profile by a source distance, a center axis of the support being parallel to the azimuthal axis of the plume spatial profile and displaced relative to the azimuthal axis of the plume spatial profile in a radial direction of the support by half a radius of the support, and
has a shape that corresponds, at the source distance, to the plume spatial profile along the radial direction of the support,
such that, when the support, with the plurality of supported instances of the substrate distributed over the support, is rotated around the center axis of the support, thicknesses of instances of each of the deposited layers are substantially uniform across the plurality of instances of the ICE.

2. The system of claim 1, wherein
the plume spatial profile $DP(x,y,z)$ is given in terms of a series expansion $$DP(x, y, z) = \sum_{j=1}^{N} d(j)A(j; x, y, z),$$

for which base functions $A(j;x,y,z)$ have respective contributions $d(j)$, $j=1-N$, and
the support shape $P(x,y,z)$ that corresponds to the plume spatial profile $DP(x,y,z)$ along the radial direction of the support is given in terms of another series expansion $$P(x, y, z) = \sum_{j=1}^{N} s(j)A(j; x, y, z),$$

for which the base the functions $A(j;x,y,z)$ have respective contributions $s(j)$, $j=1-N$, such that a difference surface of the support shape $P(x,y,z)$ and the plume spatial profile $DP(x,y,z)$ is substantially flat.

3. The system of claim 2, wherein the difference surface is flat when a first predefined threshold $\varepsilon_1$ satisfies the inequality $$\varepsilon_1 \geq \sum_{j=1}^{N} |d(j) - s(j)|.$$

4. The system of claim 2, wherein the difference surface is flat when a second predefined threshold $\varepsilon_2$ satisfies the inequality $$\varepsilon_2 \geq \sum_{j=1}^{N} (d(j) - s(j))^2.$$

5. The system of claim 2, wherein the plume spatial profile $DP(x,y,z)$ has the same spatial symmetry relative to both x and y axes.

6. The system of claim 2, wherein the plume spatial profile $DP(x,y,z)$ has a first symmetry relative to the x-axis and a second, different symmetry relative to the y-axis.

7. The system of claim 2, wherein the plume spatial profile $DP(x,y,z)$ is symmetric relative to the x-axis and is asymmetric relative to the y-axis.

8. The system of claim 2, wherein the plume spatial profile $DP(x,y,z)$ is asymmetric relative to both x and y axes.

9. The system of claim 1, wherein
the plume spatial profile is a Lambertian (cosine emission) profile, and
the support shape is an approximation of the Lambertian profile along the radial direction of the support at the source distance.

10. The system of claim 1, wherein
the plume spatial profile is a spherical profile, and
the support shape is an approximation of the spherical profile along the radial direction of the support at the source distance.

11. The system of claim 1, wherein
the plume spatial profile is a parabolic profile, and
the support shape is an approximation of the parabolic profile along the radial direction of the support at the source distance.

12. The system of claim 1, wherein
the plume spatial profile is a hyperbolic profile, and
the support shape is an approximation of the hyperbolic profile along the radial direction of the support at the source distance.

13. The system of claim 1, wherein the support shape along the radial direction of the support has continuous slope.

14. The system of claim 1, wherein the support shape along the radial direction of the support comprises two or more facets.

15. The system of claim 1, wherein the support is a circular plate.

* * * * *